(12) United States Patent
Fujiwara et al.

(10) Patent No.: US 9,816,957 B2
(45) Date of Patent: Nov. 14, 2017

(54) BLOOD COMPONENT MEASURING DEVICE, METHOD FOR MEASURING BLOOD COMPONENT, AND BIO-SENSOR

(71) Applicant: Panasonic Healthcare Holdings Co., Ltd., Tokyo (JP)

(72) Inventors: Masaki Fujiwara, Ehime (JP); Tomohiro Yamamoto, Osaka (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 341 days.

(21) Appl. No.: 14/651,125

(22) PCT Filed: Nov. 19, 2013

(86) PCT No.: PCT/JP2013/006794
§ 371 (c)(1),
(2) Date: Jun. 10, 2015

(87) PCT Pub. No.: WO2014/091682
PCT Pub. Date: Jun. 19, 2014

(65) Prior Publication Data
US 2015/0323489 A1     Nov. 12, 2015

(30) Foreign Application Priority Data

Dec. 12, 2012   (JP) .................................. 2012-271308

(51) Int. Cl.
*G01N 27/327*          (2006.01)
(52) U.S. Cl.
CPC ................................ *G01N 27/3274* (2013.01)
(58) Field of Classification Search
CPC .................................................. G01N 27/3274
See application file for complete search history.

(56) References Cited

U.S. PATENT DOCUMENTS 8,721,851 B2 *   5/2014   Uchiyama .......... G01N 27/3274
                                              204/403.01
2008/0179197 A1   7/2008   Wu
(Continued)

FOREIGN PATENT DOCUMENTS

EP       1 742 045         1/2001
EP       2 045 597         4/2009
(Continued)

OTHER PUBLICATIONS

Extended European Search Report issued in corresponding European Application No. 13863266.6, dated Oct. 9, 2015, 5 pages.
(Continued)

*Primary Examiner* — Alexander Noguerola
(74) *Attorney, Agent, or Firm* — Hamre, Schumann, Mueller & Larson, P.C.

(57) ABSTRACT

Provided is a blood component measuring device or the like that can further suppress the measurement error of a blood component. The device detects an oxidation-reduction current generated by oxidation-reduction when a first voltage is applied to a first electrode pair 21, 22 of a biosensor 1, and converts the oxidation-reduction current (glucose response value) into a glucose conversion value. The device detects a current generated when a second voltage is applied to a second electrode pair 23, 24 of the biosensor 1, and converts the detected current (blood cell amount response value) into a blood cell amount conversion value. The glucose response value is measured more than once and the blood cell amount response value is also measured more than once within a predetermined period after the introduction of the blood into the biosensor 1. A CPU 72 corrects the glucose conversion value measured within the predetermined period based on at least a part of a plurality of glucose conversion values and
(Continued)

a plurality of blood cell amount conversion values obtained from the results of measurement.

20 Claims, 14 Drawing Sheets

(56) References Cited

U.S. PATENT DOCUMENTS

| | | | |
|---|---|---|---|
| 2009/0145779 A1 | 6/2009 | Wu | |
| 2009/0301899 A1 | 12/2009 | Hodeges et al. | |
| 2010/0267161 A1* | 10/2010 | Wu | C12Q 1/001 |
| | | | 436/149 |
| 2011/0073494 A1 | 3/2011 | McColl et al. | |
| 2011/0203942 A1 | 8/2011 | Uchiyama | |
| 2012/0111739 A1* | 5/2012 | Pasqua | G01N 27/3271 |
| | | | 205/777.5 |
| 2013/0098776 A1* | 4/2013 | Hsu | G01N 27/3272 |
| | | | 205/777.5 |

FOREIGN PATENT DOCUMENTS

| | | |
|---|---|---|
| JP | 2009-294213 | 12/2009 |
| JP | 2010-540934 | 12/2010 |
| JP | 2011-506964 | 3/2011 |
| JP | 2012-108144 | 6/2012 |
| WO | 2010/061629 | 6/2010 |

OTHER PUBLICATIONS

International Search Report issued in International Application No. PCT/JP2013/006794, dated Mar. 4, 2014, 4 pages.

\* cited by examiner

| Glucose | Hct | Glu response value | Hct response value | Hct response value | Hct response value |
|---|---|---|---|---|---|
| 100mg/dl | Hct25 | 120 | 1250 | | |
| | Hct45 | 100 | 1000 | | |
| | Hct65 | 80 | 750 | | |
| 200mg/dl | Hct25 | 250 | | 1250 | |
| | Hct45 | 200 | | 1000 | |
| | Hct65 | 150 | | 750 | |
| 110mg/dl | Hct25 | 133.1 | | | 1250 |
| | Hct45 | 110 | | | 1000 |
| | Hct65 | 86.9 | | | 750 |

(a) Glucose measurement (b) Hct measurement

| Glucose conversion value=100, Blood cell amount=25 | | | | | |
|---|---|---|---|---|---|
| Ambient temperature | Sample introduction temperature (which does not need to be stored) | G1-H1 | G1-H2 | G2-H1 | G2-H2 |
| A | a | Aa1 | Aa2 | Aa3 | Aa4 |
| A | b | Ab1 | Ab2 | Ab3 | Ab4 |
| A | c | Ac1 | Ac2 | Ac3 | Ac4 |
| B | a | Ba1 | Ba2 | Ba3 | Ba4 |
| B | b | Bb1 | Bb2 | Bb3 | Bb4 |
| B | c | Bc1 | Bc2 | Bc3 | Bc4 |
| C | a | Ca1 | Ca2 | Ca3 | Ca4 |
| C | b | Cb1 | Cb2 | Cb3 | Cb4 |
| C | c | Cc1 | Cc2 | Cc3 | Cc4 |

FIG. 14

| | Response value | | | | Glucose conversion value | | | |
|---|---|---|---|---|---|---|---|---|
| | G1 | G2 | H1 | H2 | G1-H1 | G1-H2 | G2-H1 | G2-H2 |
| 25°C | 75.6 | 64.9 | 1545 | 1282 | 125 | 125 | 125 | 125 |
| 35°C | 79.5 | 67.1 | 1713 | 1303 | 120 | 122 | 131 | 129 |

FIG. 15

| | 100mg/dl | 200mg/dl | 110mg/dl |
|---|---|---|---|
| Glucose | 0.2 | 0.25 | 0.21 |
| Hct | 0.25 | 0.25 | 0.25 |

FIG. 16

|  | Original value | | Degree of influence of temperature | | Response value | |
|---|---|---|---|---|---|---|
|  | Glu | Hct | Glu | Hct | Glu | Hct |
| Case A | 100 | 1000 | 0.2 | 0.2 | 120 | 1200 |
| Case B | 100 | 1000 | 0.2 | 0.1 | 120 | 1100 |

(a) Glucose measurement (b) Hct measurement

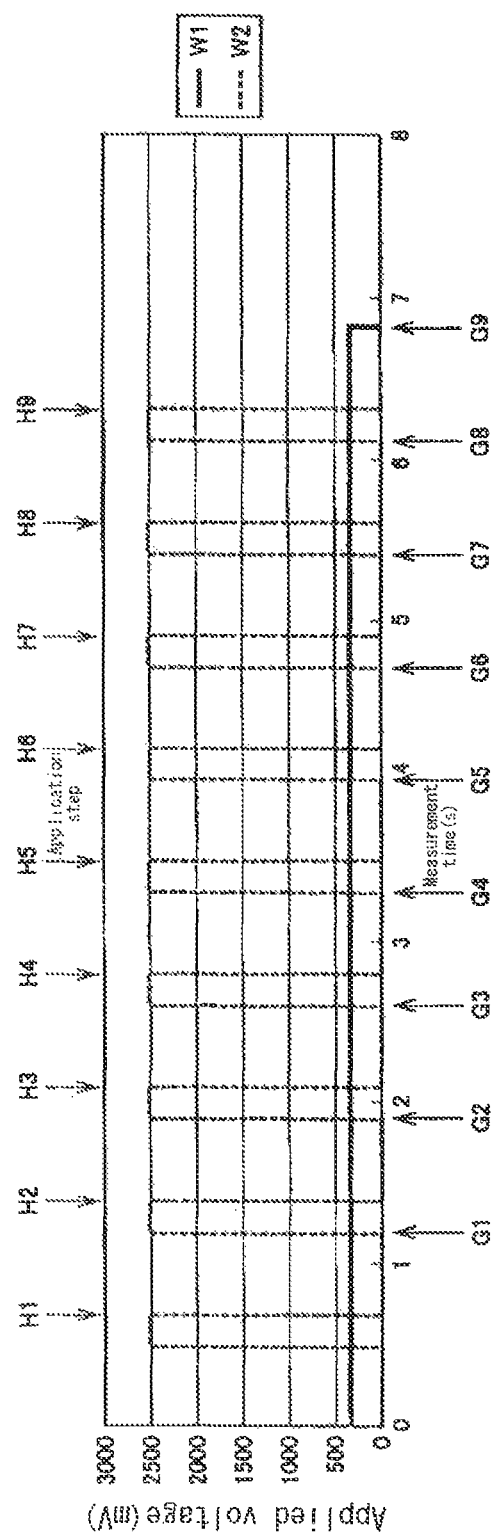
F I G. 20

BLOOD COMPONENT MEASURING DEVICE, METHOD FOR MEASURING BLOOD COMPONENT, AND BIO-SENSOR

TECHNICAL FIELD

The present invention relates to a blood component measuring device that measures a component contained in blood, a method for measuring a blood component, and a biosensor.

BACKGROUND ART

Patent Document 1 discloses a sensor system or the like for determining the concentration of an analyte in a sample. In this sensor system, input signals including multiple duty cycles of sequential excitation pulses and relaxations are input to the sample. Thus, one or more signals output from the sample within 300 ms of the input of an excitation pulse may be correlated with the analyte concentration of the sample to improve the accuracy and/or precision of the analysis.

PRIOR ART DOCUMENTS

Patent Documents

Patent Document 1: JP 2011-506964 A

DISCLOSURE OF INVENTION

Problem to be Solved by the Invention

In the above sensor system, the pulses are input to the sample more than once. However, since the analyte concentration of the sample is determined by using the output signals themselves, the measurement error cannot be fully suppressed.

The present invention has been proposed in view of the above circumstances, and it is an object of the present invention to provide a blood component measuring device, a method for measuring a blood component, and a biosensor that can further suppress the measurement error of a blood component.

Means for Solving Problem

A blood component measuring device of a first aspect of the present invention measures a blood component amount with a biosensor in which blood is introduced, and a blood component contained in the blood is oxidized and reduced by an oxidoreductase. The blood component measuring device includes the following: a blood component amount measurement means that detects an oxidation-reduction current generated by the oxidation-reduction when a first voltage is applied to a first electrode pair of the biosensor, and that converts the oxidation-reduction current into the blood component amount; a blood cell amount measurement means that detects a current generated when a second voltage is applied to a second electrode pair of the biosensor, and that converts the detected current into a blood cell amount contained in the blood; a measurement control means that controls the blood component amount measurement means to measure the blood component amount more than once within a predetermined period after the introduction of the blood into the biosensor, and that also controls the blood cell amount measurement means to measure the blood cell amount more than once within the predetermined period; and a blood component amount correction means that corrects the blood component amount measured by the blood component amount measurement means based on at least a part of a plurality of blood component amounts measured by the blood component amount measurement means and a plurality of blood cell amounts measured by the blood cell amount measurement means under the control of the measurement control means.

A blood component measuring device of a second aspect of the present invention is the blood component measuring device of the first aspect and includes a storage means. The storage means stores record data including a plurality of blood component amounts and a plurality of blood cell amounts that are converted from the respective currents detected more than once within the predetermined period for each blood with a known blood component amount and a known blood cell amount. The blood component amount correction means compares (i) the record data including a blood component amount that is closely approximated to any blood component amount of the plurality of blood component amounts measured and the plurality of blood cell amounts measured with (ii) measured data including the plurality of blood component amounts measured by the blood component amount measurement means and the plurality of blood cell amounts measured by the blood cell amount measurement means. Then, the blood component amount correction means corrects the measured blood component amount to the blood component amount of blood having the record data that is most closely approximated to the measured data.

A blood component measuring device of a third aspect of the present invention is the blood component measuring device of the second aspect and includes a storage means and a temperature detection means. The storage means stores record data including a plurality of blood component amounts and a plurality of blood cell amounts that are converted from the respective currents detected more than once within the predetermined period for each blood with a known blood component amount and a known blood cell amount and for each ambient temperature. The temperature detection means detects an ambient temperature. The blood component amount correction means extracts record data with a temperature closer to the ambient temperature detected by the temperature detection means, and compares the extracted record data with the measured data including the plurality of blood component amounts measured by the blood component amount measurement means and the plurality of blood cell amounts measured by the blood cell amount measurement means. Then, the blood component amount correction means corrects the measured blood component amount to the blood component amount of blood having the record data that is most closely approximated to the measured data.

A blood component measuring device of a fourth aspect of the present invention is the blood component measuring device of the second or third aspect. The blood component amount correction means compares (i) any combination of a blood component amount and a blood cell amount in the plurality of blood component amounts and the plurality of blood cell amounts measured under the control of the measurement control means with (ii) the record data including the same combination of a blood component amount and a blood cell amount in the plurality of blood component amounts and the plurality of blood cell amounts stored in the storage means. Then, the blood component amount correction means corrects the measured blood component amount to the blood component amount of blood having the most approximate record data.

A blood component measuring device of a fifth aspect of the present invention is the blood component measuring device of any one of the first to fourth aspects. The measurement control means controls the blood component amount measurement means to measure the blood component amount in a first period included in a first half of the predetermined period and in a second period included in a second half of the predetermined period.

A blood component measuring device of a sixth aspect of the present invention is the blood component measuring device of the fifth aspect. The measurement control means controls the blood component amount measurement means to measure the blood component amount at least in a first period of the predetermined period during which a change in temperature of the blood introduced into the biosensor is large and in a second period of the predetermined period during which a change in temperature of the blood introduced into the biosensor is stable.

A blood component measuring device of a seventh aspect of the present invention is the blood component measuring device of the fifth or sixth aspect. The measurement control means controls the blood cell amount measurement means to measure the blood cell amount at least in the first period and in the second period, during each of which the blood component amount is measured by the blood component amount measurement means.

A blood component measuring device of an eighth aspect of the present invention is the blood component measuring device of any one of the fifth to seventh aspects. The record data and the measured data include the following: a group of the blood component amount measured in the first period and the blood cell amount measured in the first period; a group of the blood component amount measured in the first period and the blood cell amount measured in the second period; a group of the blood component amount measured in the second period and the blood cell amount measured in the first period; and a group of the blood component amount measured in the second period and the blood cell amount measured in the second period. The blood component amount correction means compares the same group between the record data and the measured data.

A blood component measuring device of a ninth aspect of the present invention is the blood component measuring device of any one of the first to eighth aspects. The measurement control means controls the blood component amount measurement means to apply the first voltage to the first electrode pair within the predetermined period, and to detect an oxidation-reduction current corresponding to the blood component amount more than once at predetermined timing of measurement of the blood component amount. The measurement control means also controls the blood cell amount measurement means to apply the second voltage to the second electrode pair in a predetermined state before, during, or after the predetermined timing of the measurement of the blood component amount, and to detect a current corresponding to the blood cell amount.

A blood component measuring device of a tenth aspect of the present invention is the blood component measuring device of the first aspect. The blood component amount correction means performs a multivariate analysis with the use of at least a part of the plurality of blood component amounts and the plurality of blood cell amounts to correct the blood component amount measured by the blood component amount measurement means.

A method for measuring a blood component of an eleventh aspect of the present invention measures a blood component amount with a biosensor in which blood is introduced, and a blood component contained in the blood is oxidized and reduced by an oxidoreductase. The method includes the following steps of (i) detecting an oxidation-reduction current generated by the oxidation-reduction when a first voltage is applied to a first electrode pair of the biosensor, and converting the oxidation-reduction current into the blood component amount; and (ii) detecting a current generated when a second voltage is applied to a second electrode pair of the biosensor, and converting the detected current into a blood cell amount contained in the blood. The blood component amount is measured more than once within a predetermined period after the introduction of the blood into the biosensor, and the blood cell amount is measured more than once within the predetermined period. The measured blood component amount is corrected based on at least a part of the plurality of blood component amounts measured and the plurality of blood cell amounts measured.

A method for measuring a blood component of a twelfth aspect of the present invention is the method for measuring a blood component of the eleventh aspect. The method includes the following: referring to record data including a plurality of blood component amounts and a plurality of blood cell amounts that are converted from the respective currents detected more than once within the predetermined period for each blood with a known blood component amount and a known blood cell amount stored in a storage means; comparing (i) the record data including a blood component amount that is closely approximated to any blood component amount of the plurality of blood component amounts measured and the plurality of blood cell amounts measured with (ii) measured data including the plurality of blood component amounts measured and the plurality of blood cell amounts measured; and correcting the measured blood component amount to the blood component amount of blood having the record data that is most closely approximated to the measured data.

A method for measuring a blood component of a thirteenth aspect of the present invention is the method for measuring a blood component of the twelfth aspect. The method includes the following: referring to record data including a plurality of blood component amounts and a plurality of blood cell amounts that are converted from the respective currents detected more than once within the predetermined period for each blood with a known blood component amount and a known blood cell amount and for each ambient temperature stored in a storage means; detecting an ambient temperature; extracting record data with a temperature closer to the detected ambient temperature, and comparing the extracted record data with measured data including the plurality of blood component amounts measured and the plurality of blood cell amounts measured; and correcting the measured blood component amount to the blood component amount of blood having the record data that is most closely approximated to the measured data.

A method for measuring a blood component of a fourteenth aspect of the present invention is the method for measuring a blood component of the twelfth or thirteenth aspect. The method includes the following: comparing (i) any combination of a blood component amount and a blood cell amount in the plurality of blood component amounts measured and the plurality of blood cell amounts measured with (ii) the record data including the same combination of a blood component amount and a blood cell amount in the plurality of blood component amounts and the plurality of blood cell amounts stored in the storage means; and correcting the measured blood component amount to the blood component amount of blood having the most approximate record data.

A method for measuring a blood component of a fifteenth aspect of the present invention is the method for measuring a blood component of any one of the eleventh to fourteenth aspects. The method includes measuring the blood component amount in a first period included in a first half of the predetermined period and in a second period included in a second half of the predetermined period.

A method for measuring a blood component of a sixteenth aspect of the present invention is the method for measuring a blood component of the fifteenth aspect. The method includes measuring the blood component amount at least in a first period of the predetermined period during which a change in temperature of the blood introduced into the biosensor is large and in a second period of the predetermined period during which a change in temperature of the blood introduced into the biosensor is stable.

A method for measuring a blood component of a seventeenth aspect of the present invention is the method for measuring a blood component of the fifteenth or sixteenth aspect. The method includes measuring the blood cell amount at least in the first period and in the second period.

A method for measuring a blood component of an eighteenth aspect of the present invention is the method for measuring a blood component of any one of the fifteenth to seventeenth aspects. The record data and the measured data include a group of the blood component amount measured in the first period and the blood cell amount measured in the first period, a group of the blood component amount measured in the first period and the blood cell amount measured in the second period, a group of the blood component amount measured in the second period and the blood cell amount measured in the first period, and a group of the blood component amount measured in the second period and the blood cell amount measured in the second period. The blood component amount is corrected by comparing the same group between the record data and the measured data.

A method for measuring a blood component of a nineteenth aspect is the method for measuring a blood component of any one of the eleventh to eighteenth aspects. The method includes the following: applying the first voltage to the first electrode pair within the predetermined period, and detecting an oxidation-reduction current corresponding to the blood component amount more than once at predetermined timing of measurement of the blood component amount; and applying the second voltage in pulses to the second electrode pair within a predetermined short time before, during, or after the predetermined timing of the measurement of the blood cell amount and only at timing of measurement of the blood component amount in the predetermined period, and detecting a current corresponding to the blood cell amount.

A method for measuring a blood component of a twentieth aspect of the present invention is the method for measuring a blood component of the eleventh aspect. The method includes performing a multivariate analysis with the use of at least a part of the plurality of blood component amounts and the plurality of blood cell amounts to correct the blood component amount measured within the predetermined period.

A biosensor of a twenty-first aspect of the present invention is a biosensor in which blood is introduced, and a blood component contained in the blood is oxidized and reduced by an oxidoreductase. The biosensor includes the following: a blood component amount measuring electrode pair including a working electrode and a counter electrode that are in contact with the oxidoreductase and a mediator; a blood cell amount measuring electrode pair including a working electrode that is not in contact with the oxidoreductase and a mediator, and a counter electrode that is in contact with the oxidoreductase and a mediator, but not in contact with the working electrode of the blood component amount measuring electrode pair; and a non-interacting portion that separates the working electrode of the blood component amount measuring electrode pair from the counter electrode of the blood cell amount measuring electrode pair. A first voltage is applied to the blood component amount measuring electrode pair to measure a blood component amount of the blood that has been introduced into the working electrode and the counter electrode of the blood component amount measuring electrode pair, and a second voltage is applied in pulses to the blood cell amount measuring electrode pair to measure a blood cell amount contained in the blood that has been introduced into the counter electrode of the blood cell amount measuring electrode pair.

A biosensor of a twenty-second aspect of the present invention is a biosensor in which in which blood is introduced, and a blood component contained in the blood is oxidized and reduced by an oxidoreductase. The biosensor includes the following: a blood component amount measuring electrode pair including a working electrode and a counter electrode that are in contact with the oxidoreductase and a mediator; a blood cell amount measuring electrode pair including a working electrode that is not in contact with the oxidoreductase and a mediator, and a counter electrode that is in contact with the oxidoreductase and a mediator, but not in contact with the working electrode of the blood component amount measuring electrode pair; and a non-interacting portion that separates the working electrode of the blood component amount measuring electrode pair from the counter electrode of the blood cell amount measuring electrode pair.

Effects of the Invention

In the present invention, since the measured blood component amount is corrected by using the conversion values of a plurality of blood component amounts and the conversion values of a plurality of blood cell amounts, the measurement error of the blood component can be suppressed compared to the correction of the blood component amount by using the response values themselves.

BRIEF DESCRIPTION OF DRAWINGS

FIG. 7A is a diagram showing a change in voltage for obtaining the glucose response value. FIG. 7B is a diagram showing a change in voltage for obtaining the blood cell amount response value.

FIG. 14 is a diagram showing the relationship between the ambient temperature, the sample introduction temperature, and the glucose conversion value in a measuring device according to an embodiment of the present invention.

FIG. 15 is a diagram showing the relationship between the glucose response value, the blood cell amount response value, and the glucose conversion value at each temperature of a measuring device according to an embodiment of the present invention.

FIG. 16 is a diagram showing the degree of the influence of the glucose conversion value on the blood cell amount conversion value in a measuring device according to an embodiment of the present invention.

FIG. 19A is a diagram showing a change in voltage for obtaining the glucose response value. FIG. 19B is a diagram showing a change in voltage for obtaining the blood cell amount response value.

FIG. 20 is a diagram showing timing of the measurement of the glucose response value and the blood cell amount response value by a measuring device according to an embodiment of the present invention.

DESCRIPTION OF THE INVENTION

Hereinafter, embodiments of the present invention will be described with reference to the drawings.

First, a biosensor 1 will be described.

Figure 1:
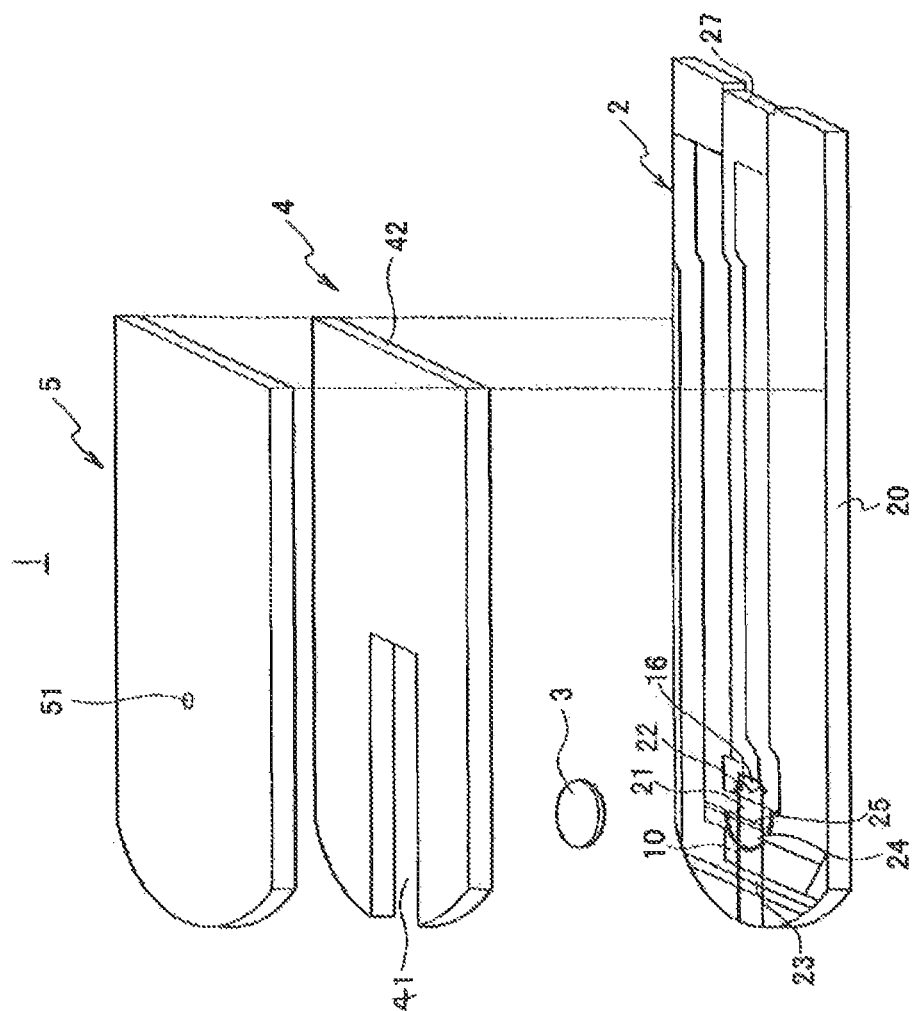
FIG. 1 is an exploded perspective view of a biosensor according to an embodiment of the present invention.
Figure 2:
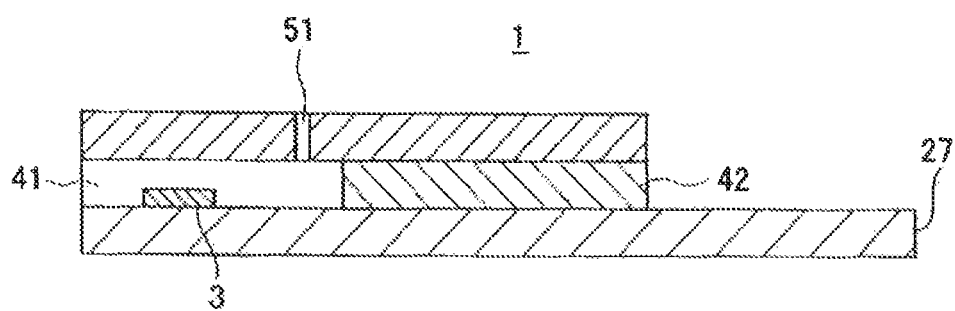
FIG. 2 is a cross-sectional view of a biosensor according to an embodiment of the present invention.
Figure 3:
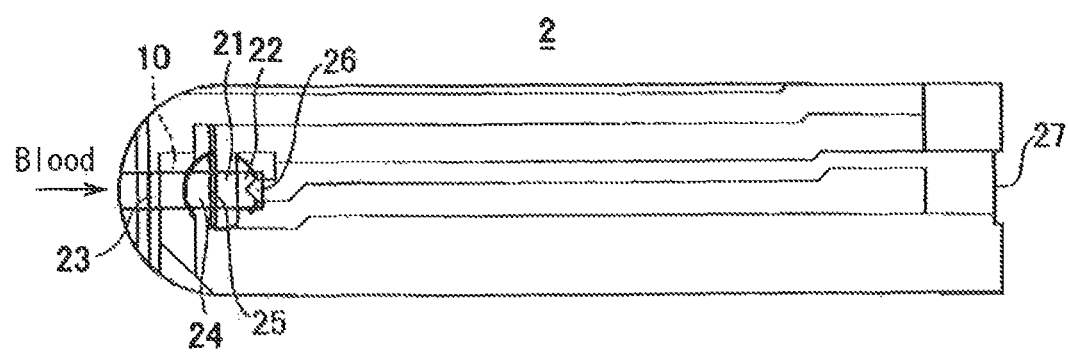
FIG. 3 is a top view of a blood component measurement layer of a biosensor according to an embodiment of the present invention.

The biosensor 1 according to an embodiment of the present invention includes portions as shown in, e.g., FIGS. 1 to 3. FIG. 1 is an exploded perspective view of the biosensor 1. FIG. 2 is a cross-sectional view of the biosensor 1. The biosensor 1 includes a blood component measurement layer 2, a reagent layer 3, a spacer layer 4, and a surface layer 5. These layers are laminated to form the biosensor 1. In the following, the biosensor 1 will be described as a biosensor for measuring glucose as a blood cell component, but is not limited thereto.

The biosensor 1 is removably attached to a measuring device 6, which will be described later. The biosensor 1 and the measuring device 6 constitute a biosensor system. In the biosensor system, a drop of blood (sample) is placed on a sample placement portion 41 that is located on the front end of the biosensor 1, and the amount of a component of a substrate contained in the blood (sample) is measured by the measuring device 6. As a result of the measurement, the measuring device 6 displays the measured blood component amount.

When the biosensor 1 is used to quantify the blood component amount in blood, first, a user inserts an end portion 27 of the biosensor 1 into the measuring device 6. Then, the measuring device 6 applies a voltage to electrodes of the biosensor 1, as will be described later. In this state, blood is supplied to the sample placement portion 41. Subsequently, a drop of blood is placed and drawn into the biosensor 1. The reagent layer 3 is dissolved with this blood. The measuring device 6 detects an electrical change that occurs between the electrodes of the biosensor 1, and measures the blood component amount.

In this embodiment, the biosensor 1 measures a specific blood component amount contained in human blood (sample liquid). The specific blood component amount includes a glucose concentration. The following explanation relates to the measurement of the glucose concentration in human blood. However, the biosensor system of this embodiment can also measure lactic acid, cholesterol, and any other components by selecting appropriate enzymes.

The blood component measurement layer 2 includes an insulating substrate 20 and a conductive layer formed on the insulating substrate 20. The insulating substrate 20 is made of, e.g., polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylate resin (PMMA), ABS resin (ABS), or glass. The conductive layer is made of, e.g., noble metals such as gold, platinum, and palladium or electrically conductive materials such as carbon. The conductive layer is formed by, e.g., screen printing or sputtering. The conductive layer may be provided on the entire surface or at least a part of the surface of the substrate. The conductive layer may be coated with a polymeric material in order to prevent adhesion of impurities, oxidation, or the like. The coating on the surface of the conductive layer can be performed, e.g., by preparing a solution of the polymeric material, dropping or applying the solution to the surface of the conductive layer, and drying the solution. The drying process is, e.g., natural drying, air drying, hot air drying, or drying by heating.

The size of the insulating substrate 20 is not particularly limited. For example, the insulating substrate 20 has a total length of 5 to 100 mm, a width of 2 to 50 mm, and a thickness of 0.05 to 2 mm, preferably has a total length of 7 to 50 mm, a width of 3 to 20 mm, and a thickness of 0.1 to 1 mm, and more preferably has a total length of 10 to 30 mm, a width of 3 to 10 mm, and a thickness of 0.1 to 0.6 mm.

The material of the spacer layer 4 is not particularly limited and may be, e.g., the same as that of the substrate 20. The size of the spacer layer 4 is not particularly limited. For example, the spacer layer 4 has a total length of 5 to 100 mm, a width of 2 to 50 mm, and a thickness of 0.01 to 1 mm, preferably has a total length of 7 to 50 mm, a width of 3 to 20 mm, and a thickness of 0.05 to 0.5 mm, and more preferably has a total length of 10 to 30 mm, a width of 3 to 10 mm, and a thickness of 0.05 to 0.25 mm. The spacer layer 4 has an I-shaped notch that serves as the sample placement portion 41 for the introduction of blood.

The surface layer 5 is an insulating substrate having an air hole 51 in the center. The surface layer 5 is integrally disposed with the blood component measurement layer 2 so that the spacer layer 4 having the sample placement portion 41 (notch) is sandwiched between the surface layer 5 and the blood component measurement layer 2. In order to integrally dispose the layers, the surface layer 5, the spacer layer 4, and the blood component measurement layer 2 may be joined using an adhesive or thermally fused together. Examples of the adhesive include an epoxy adhesive, an acrylic adhesive, a polyurethane adhesive, a thermosetting adhesive (such as a hot-melt adhesive), and a UV curable adhesive.

The material of the surface layer 5 is not particularly limited and may be, e.g., the same as that of the substrate 20. It is more preferable that a portion of the surface layer 4 that corresponds to the ceiling of the sample placement portion 41 is subjected to a hydrophilic treatment. The hydrophilic treatment may be, e.g., a method for applying a surface active agent to the surface of the surface layer 5 or a method for introducing a hydrophilic functional group such as a hydroxyl group, a carbonyl group, or a carboxyl group into the surface of the surface layer 5 by plasma processing. The size of the surface layer 5 is not particularly limited. For example, the surface layer 5 has a total length of 5 to 100 mm, a width of 3 to 50 mm, and a thickness of 0.01 to 0.5 mm, preferably has a total length of 10 to 50 mm, a width of 3 to 20 mm, and a thickness of 0.05 to 0.25 mm, and more preferably has a total length of 15 to 30 mm, a width of 5 to 10 mm, and a thickness of 0.05 to 0.1 mm. The cover 12 preferably has the air hole 15, e.g., in the form of a circle, an ellipse, or a polygon. The air hole 51 has, e.g., a maximum diameter of 0.01 to 10 mm, preferably a maximum diameter of 0.05 to 5 mm, and more preferably a maximum diameter of 0.1 to 2 mm.

As shown in FIG. 3, a plurality of slits are provided in the conductive layer on the substrate 20, thereby forming various electrodes of the blood component measurement layer 2. FIG. 3 is a top view of the blood component measurement layer 2 of the biosensor 1. The blood component measurement layer 2 includes a glucose working electrode 21 and a glucose counter electrode 22 to measure the glucose concentration. The glucose working electrode 21 and the glucose counter electrode 22 are located at the positions where they are in contact with an oxidoreductase and a mediator of the reagent layer 3, as will be described later. The blood component measurement layer 2 includes a blood cell amount working electrode 23 and a blood cell amount counter electrode 24 to measure the blood cell amount. The blood cell value working electrode 23 is located at the position where it is not in contact with the oxidoreductase and the mediator of the reagent layer 3, as will be described later. The blood cell amount counter electrode 24 is located at the position where it is in contact with the oxidoreductase and the mediator of the reagent layer 3, as will be described later, but not in contact with the glucose working electrode 21. Moreover, the blood component measurement layer 2 includes a detecting electrode 26 to detect the introduction of blood. The glucose working electrode 21, the glucose counter electrode 22, the blood cell amount working electrode 23, the blood cell amount counter electrode 24, and the detecting electrode 26 are electrically connected to the measuring device 6 while the biosensor 1 is being inserted into the measuring device 6.

To measure the glucose concentration, a voltage (first voltage) is applied between the glucose working electrode 21 as a positive electrode and the glucose counter electrode 22 as a negative electrode. The glucose working electrode 21 and the glucose counter electrode 22 function as a blood component amount measuring electrode pair. To measure the blood cell amount, a voltage (second voltage) is applied in pulses between the blood cell amount working electrode 23 as a positive electrode and the blood cell amount counter electrode 24 as a negative electrode. The blood cell amount working electrode 23 and the blood cell amount counter electrode 24 function as a blood cell amount measuring electrode pair. The pulses may be in the form of a rectangular wave or a triangular wave. The details of the application of these voltages will be described later.

A non-interacting portion 25 in which the conductive layer is not formed is provided between the glucose working electrode 21 and the blood cell amount counter electrode 24. The non-interacting portion 25 separates the glucose working electrode 21 from the blood cell amount counter electrode 24. Thus, the non-interacting portion 25 prevents the mediator generated in the blood cell amount counter electrode 24 from flowing into the glucose working electrode 21 during the measurement of the blood cell amount.

In the blood component measurement layer 2, an identification portion may be formed by the electrode in order for the measuring device 6 to identify the biosensor 1. The identification portion may have a shape, e.g., for identifying the type of the biosensor 1 or the difference in the output characteristics of the production lots. The identification portion is formed, e.g., on the end portion 27 side of the biosensor 1 and can be read by the measuring device 6.

As shown in FIG. 1, the spacer layer 4 is disposed to cover each of the electrodes 21 to 24, 26 on the substrate 20 of the blood component measurement layer 2. The spacer layer 4 is a substrate 42 having the rectangular sample placement portion 41 provided in the center of the front end. The sample placement portion 41 forms a sample supply path 10 shown in FIG. 3. When a drop of blood is placed on the sample placement portion 41, the blood is drawn in the right direction of FIGS. 1 to 3 toward the air hole 51 of the surface layer 5 by a capillary action. Consequently, the blood is introduced into the glucose working electrode 21, the glucose counter electrode 22, the blood cell amount working electrode 23, and the blood cell amount counter electrode 24.

As shown in FIG. 1, the reagent layer 3 is arranged between the blood component measurement layer 2 and the spacer layer 4. The reagent layer 3 is formed by the application of a reagent containing, e.g., an enzyme, a mediator (electron receptor), an amino acid, and sugar alcohol. The reagent layer 3 is in contact with the glucose working electrode 21 and the glucose counter electrode 22 that are exposed from the sample placement portion 41 of the spacer layer 4. The reagent layer 3 selectively includes a polymeric material, an enzyme stabilizer, and a crystal homogenizing agent as optional components. The surface layer 5 is disposed on the blood component measurement layer 2 and the reagent layer 3 via the spacer layer 4, while leaving one end of the blood component measurement layer 2 uncovered.

Examples of the oxidoreductase of the reagent layer 3 include the following: glucose oxidase; lactate oxidase; cholesterol oxidase; cholesterol esterase; uricase; ascorbate oxidase; bilirubin oxidase; glucose dehydrogenase; lactate dehydrogenase; and lactate dehydrogenase. The amount of the oxidoreductase is, e.g., 0.01 to 100 U, preferably 0.05 to 10 U, and more preferably 0.1 to 5 U per one biosensor or one measurement. In particular, glucose oxidase and glucose dehydrogenase are preferred as the oxidoreductase.

The mediator (electron receptor) of the reagent layer 3 is preferably ferricyanide, and more preferably potassium ferricyanide. In addition to the ferricyanide, the other mediators may include, e.g., p-benzoquinone and its derivative, phenazine methosulfate, methylene blue, and ferrocene and its derivative. The amount of the electron carrier mixed is not particularly limited and may be, e.g., 0.1 to 1000 mM, preferably 1 to 500 mM, and more preferably 10 to 200 mM per one measurement or one biosensor.

To measure, e.g., the glucose concentration (blood component) in human blood, the biosensor 1 of this embodiment uses glucose oxidase as the oxidoreductase and potassium ferricyanide as the mediator, which are carried by the reagent layer 3.

When blood is introduced into the sample supply path 10, the oxidoreductase and the mediator of the reagent layer 3 are dissolved in the blood (sample liquid). Then, an enzyme reaction with glucose (i.e., the substrate) in the blood proceeds, and the mediator is reduced to form ferrocyanide (potassium ferrocyanide in this embodiment). After the completion of this reaction, the reduced mediator is oxidized electrochemically, and the resultant current is used to measure the glucose concentration (glucose response value) in the blood.

In the present invention, the blood cells mean red blood cells, white blood cells, platelets, and their combinations contained in blood, and preferably mean red blood cells. In the present invention, the blood cell amount means, e.g., the ratio (volume ratio) of red blood cells in blood, and preferably means a hematocrit (Hct) value.

Next, the configuration of the measuring device 6 will be described.

Figure 4:
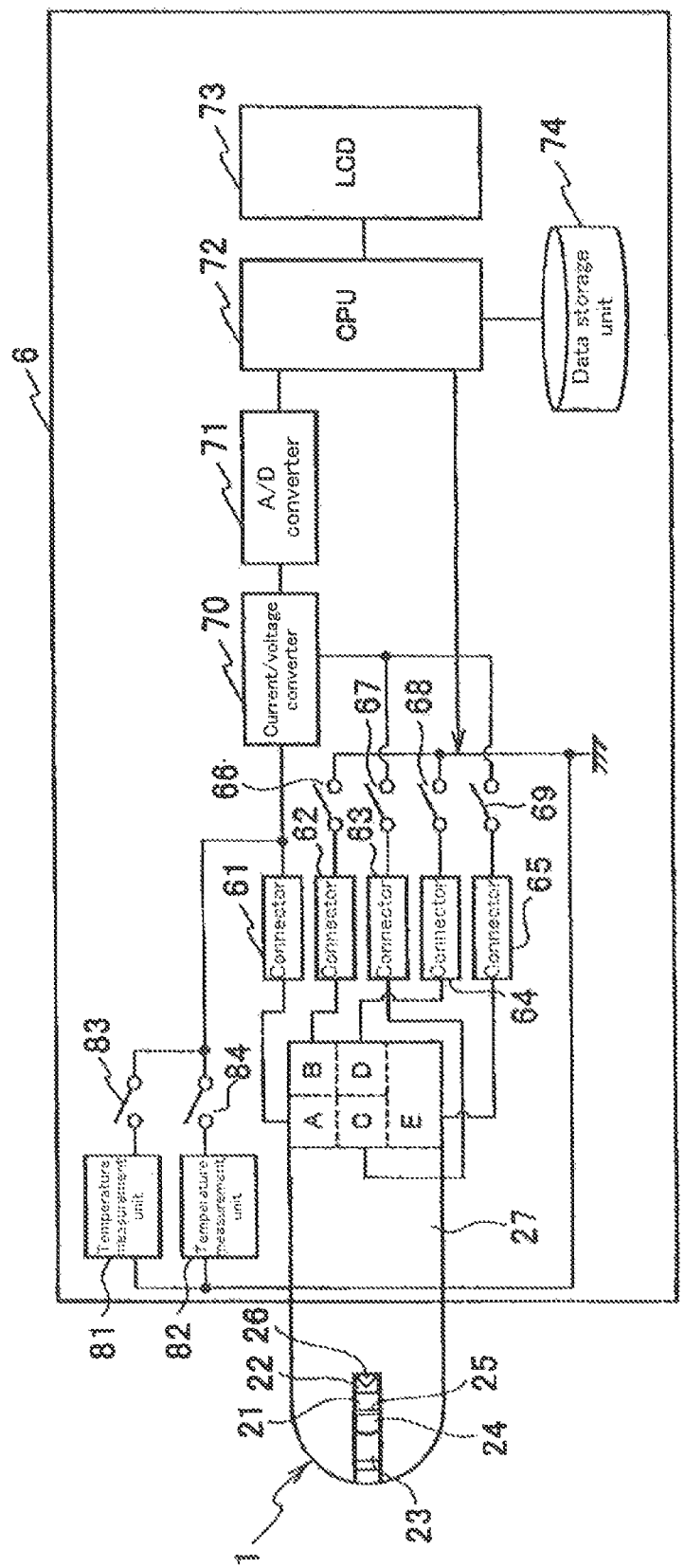
FIG. 4 is a block diagram showing a configuration of a measuring device according to an embodiment of the present invention.

The measuring device 6 measures the glucose concentration (blood component amount) with the biosensor 1 in which blood is introduced, and a blood component contained in the blood is oxidized and reduced by the oxidoreductase. As shown in FIG. 4, when the biosensor 1 is inserted into the measuring device 6, the measuring device 6 is connected to the electrodes A to E provided in the end portion 27 of the biosensor 1. The electrode A corresponds to the glucose working electrode 21, the electrode B corresponds to the glucose counter electrode 22, the electrode C corresponds to the blood cell amount working electrode 23, the electrode D corresponds to the blood cell amount counter electrode 24, and the electrode E corresponds to the detecting electrode 26.

The measuring device 6 includes a plurality of connectors 61 to 65, a plurality of switches 66 to 69, a current/voltage converter 70, an A/D converter 71, a CPU 72, an LCD 73, and a data storage unit 74 (storage means). Moreover, the measuring device 6 includes temperature measurement units 81, 82 for measuring the temperature in the device and switches 83, 84 for the temperature measurement units 81, 82. The connectors 62, 64 and the switches 67, 68 are connected to the glucose counter electrode 22 (negative electrode) and the blood cell amount counter electrode 24 (negative electrode), respectively, and are grounded.

Each of the temperature measurement units 81, 82 measures the temperature in the measuring device 6 as an ambient temperature of blood introduced. For example, it is desirable that the temperature measurement units 81, 82 measure the temperature in the position closer to the biosensor 1 inserted into the measuring device 6. The temperature values measured by the temperature measurement units 81, 82 are supplied to the CPU 72. The CPU 72 compares the two measured temperature values. If a difference between the temperature values is not within a predetermined threshold value, the CPU 72 determines that either the temperature measurement unit 81 or 82 has broken down. This makes it easy and accurate to detect a failure of the measuring device 6. Moreover, this can avoid a measurement error due to an irregular temperature measurement. The timing of the temperature measurement may be the time immediately after the introduction of blood is detected by the detecting electrode 26, or the time when the temperature of blood introduced into the biosensor 1 becomes stable.

The connectors 61 to 65 are connected to the electrodes A to E of the biosensor 1, respectively. The switches 66 to 69 are connected to the connectors 62 to 65, respectively. The ON and OFF states of the switches 66 to 69 are controlled by the CPU 72. To measure the glucose concentration, the switch 66 is turned on so that a voltage is applied between the electrode A connected to the glucose working electrode 21 and the electrode B connected to the glucose counter electrode 22. To measure the blood cell amount, the switches 67, 68 are turned on so that a voltage is applied between the electrode C connected to the blood cell amount working electrode 23 and the electrode D connected to the blood cell amount counter electrode 24. Both the voltage applied between the glucose working electrode 21 and the glucose counter electrode 22 and the voltage applied between the blood cell amount working electrode 23 and the blood cell amount counter electrode 24 can be changed. To detect the introduction of blood, the switch 69 is turned on so that a voltage is applied to the electrode E connected to the detecting electrode 26.

The current/voltage converter 70 is connected to the connectors 61 to 65 and the temperature measurement units 81, 82. The current flowing between the glucose working electrode 21, the blood cell amount working electrode 23, and the other electrodes is supplied to the current/voltage converter 70. Moreover, the current corresponding to the ambient temperature measured by the temperature measurement units 81, 82 is supplied to the current/voltage converter 70. The current/voltage converter 70 converts the supplied current into a voltage. Then, the voltage value is supplied to the A/D converter 71.

The voltage value from the current/voltage converter 70 is supplied to the A/D converter 71. The A/D converter 71 converts the supplied voltage value into digital data in the form of pulses, and outputs the digital data to the CPU 72.

The CPU 72 controls each of the units included in the measuring device 6. The CPU 72 performs on-off control of the switches 66 to 69. Moreover, the CPU 72 calculates a glucose response value and a blood cell amount response value of blood based on the digital data from the A/D converter 71. The CPU 72 converts the calculated glucose response value and the calculated blood cell amount response value into a glucose conversion value and a blood cell amount conversion value. In this case, the CPU 72 converts the calculated glucose response value and the calculated blood cell amount response value based on a glucose response value and a blood cell amount response value of blood whose glucose concentration and blood cell amount have been known. The process of converting the glucose response value and the blood cell amount response value into the glucose conversion value and the blood cell amount conversion value will be described later.

The LCD 73 is an LCD (liquid crystal display: output unit) for displaying the measured values calculated by the CPU 72.

The data storage unit 74 stores data that can be referred to by the CPU 72. The data storage unit 74 stores record data, with which the CPU 72 corrects the glucose conversion value. The record data may include glucose conversion values (blood component amounts) and blood cell value conversion values that are converted from the respective currents measured more than once within a predetermined period for each blood with a known glucose concentration (blood component amount) and a known blood cell amount. Moreover, the record data may include glucose conversion values and blood cell value conversion values that are measured more than once within the predetermined period for each blood with a known glucose concentration and a known blood cell amount and for each ambient temperature. Further, the record data may include any combinations of glucose conversion values and blood cell value conversion values that are measured more than once for each blood with a known glucose concentration and a known blood cell amount. Further, the record data may include any combinations of glucose conversion values and blood cell value conversion values that are measured more than once for each blood with a known glucose concentration and a known blood cell amount and for each ambient temperature.

Next, a basic operation of the measuring device 6 will be described.

When the measuring device 6 measures the glucose concentration and the blood cell amount, first, the introduction of blood is detected by the detecting electrode 26.

In the measuring device 6, to measure the glucose concentration, the CPU 72 turns the switch 66 on so that a voltage (first voltage) is applied between the glucose working electrode 21 and the glucose counter electrode 22 (first electrode pair). In this state, the CPU 72 detects an oxidation-reduction current (glucose response value) generated by oxidation-reduction, and converts the oxidation-reduction current into a glucose conversion value (blood component amount measurement means). The conversion process of the glucose response value will be described later.

In the measuring device 6, to measure the blood cell amount, the CPU 72 turns the switches 67, 68 on so that a voltage (second voltage) is applied between the blood cell amount working electrode 23 and the blood cell amount counter electrode 24 (second electrode pair). In this state, the CPU 72 detects a current (blood cell value response value) generated by the application of the voltage to the blood cell amount working electrode 23 and the blood cell amount counter electrode 24, and converts the detected current into a blood cell value conversion value contained in the blood (blood cell amount measurement means).

The CPU 72 measures the glucose response value and the blood cell value response value within a predetermined period after the introduction of the blood into the biosensor 1. The predetermined period can be set to, e.g., 5 seconds or 7 seconds. The CPU 72 controls the measurement in such a manner that the glucose response value is measured more than once and the blood cell amount response value is measured more than once within the predetermined period (measurement control means). Therefore, the CPU 72 may perform on-off control of the switches 66 to 68 according to the timing of the measurement. The CPU 72 may also control the timing of the acquisition of digital data by the A/D converter 71.

The CPU 72 corrects the measured glucose conversion value based on at least a part of a plurality of glucose conversion values and a plurality of blood cell value conversion values (blood component amount correction means). The glucose conversion value (blood component amount) to be corrected is, e.g., a glucose conversion value measured at the end of the predetermined period. The glucose conversion value to be corrected may be any value measured during the predetermined period rather than the value measured at the end of the predetermined period. In this case, the CPU 72 refers to the record data. As the blood component amount correction means, the CPU 72 compares the record data including a plurality of glucose conversion values and a plurality of blood cell value conversion values stored in the data storage unit 74 with the measured data including a plurality of glucose conversion values and a plurality of blood cell value conversion values. The CPU 72 corrects any glucose conversion value measured during the predetermined period to the glucose concentration of blood having the record data that is most closely approximated to the measured data.

In the measuring device 6, when the data storage unit 74 stores the record data including a plurality of glucose conversion values and a plurality of blood cell value conversion values for each ambient temperature, the ambient temperature may be measured by the temperature measurement units 81, 82 and the record data with the measured ambient temperature may be used. The measuring device 6 compares the record data including a plurality of glucose conversion values and a plurality of blood cell value conversion values corresponding to the measured ambient temperature with the measured data including a plurality of glucose conversion values and a plurality of blood cell value conversion values. Thus, the measuring device 6 can correct the glucose conversion value of the measured data to the glucose concentration of blood having the record data that is most closely approximated to the measured data.

In the measuring device 6, when the data storage unit 74 stores the record data including any combinations of glucose conversion values and blood cell value conversion values, the measured data including the same combinations of glucose conversion values and blood cell value conversion values as those of the record data may be used. The measuring device 6 compares the record data including any combinations of the glucose conversion values and the blood cell value conversion values with the measured data including the same combinations of the glucose conversion values and the blood cell value conversion values as those of the record data. Thus, the measuring device 6 can correct the glucose conversion value of the measured data to the glucose concentration of blood having the record data that is most closely approximated to the measured data.

Next, an operation of the measuring device 6 to convert the glucose response value and the blood cell amount response value into the glucose conversion value and the blood cell amount conversion value will be described.

In the measuring device 6, the glucose concentration is supplied to the CPU 72 as a glucose response value that is a current value, a voltage value, and digital data that are proportional to the glucose concentration. The glucose response value that is expected to be supplied to the CPU 72 is shown in, e.g., FIG. 5. For example, when the glucose concentration is 100 mg/dl and the blood cell amount (Hct) is 25%, the CPU 72 is expected to receive a glucose response value (current value) of 120 and a blood cell value response value (current value) of 1250. Such predicted values of the glucose response value and the blood cell amount response value can be obtained by preparing blood in which the glucose concentration and the blood cell amount have previously been adjusted, and measuring the blood with the biosensor 1 and the measuring device 6.

Figures 5, 6:
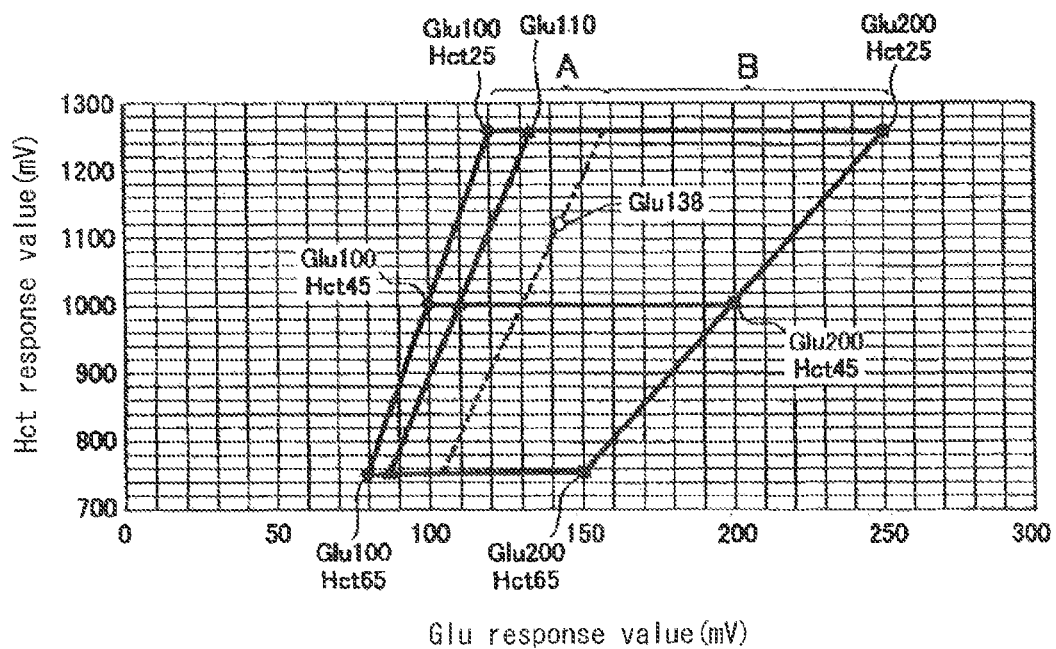
FIG. 5 is a diagram showing the glucose response value and the blood cell amount response value with respect to a known glucose concentration and a known blood cell amount.
FIG. 6 is a diagram showing the relationship between the glucose response value and the blood cell amount response value.

The glucose response values and the blood cell amount response values shown in FIG. 5, which are obtained from blood with a known glucose concentration and a known blood cell amount, are plotted on a graph, and then the points plotted on the graph are joined to form lines, resulting in a glucose concentration conversion matrix as shown in FIG. 6. The glucose concentration conversion matrix shows that the glucose response value of blood varies with different blood cell amounts even if the glucose concentration is the same.

In the glucose concentration conversion matrix, any glucose response value plotted on the line containing the points derived from the same known glucose concentration can be converted into the known glucose concentration. Therefore, by using the glucose concentration conversion matrix, the glucose conversion value can be obtained from the glucose response value and the blood cell amount response value of unknown blood. For example, when the glucose response value and the blood cell amount response value are given as indicated by a white circle in FIG. 6, the ratio (A:B) of the glucose response value at 100 mg/dl to the glucose response value at 200 mg/dl in the glucose concentration conversion matrix is determined, and thus the glucose conversion value of 138 mg/dl can be obtained.

Similarly, in the glucose concentration conversion matrix, any blood cell amount response value plotted on the line containing the points derived from the same known blood cell amount can be converted into the known blood cell amount. Therefore, by using the glucose concentration conversion matrix, the blood cell amount response value can be obtained from the glucose response value and the blood cell amount response value of unknown blood.

As described above, the use of the glucose concentration conversion matrix can provide the glucose conversion value and the blood cell amount conversion value from the glucose response value and the blood cell amount response value.

Next, an operation of the measuring device 6 to correct the glucose conversion value of the measured data by comparing the record data with the measured data will be described.

Figure 7:
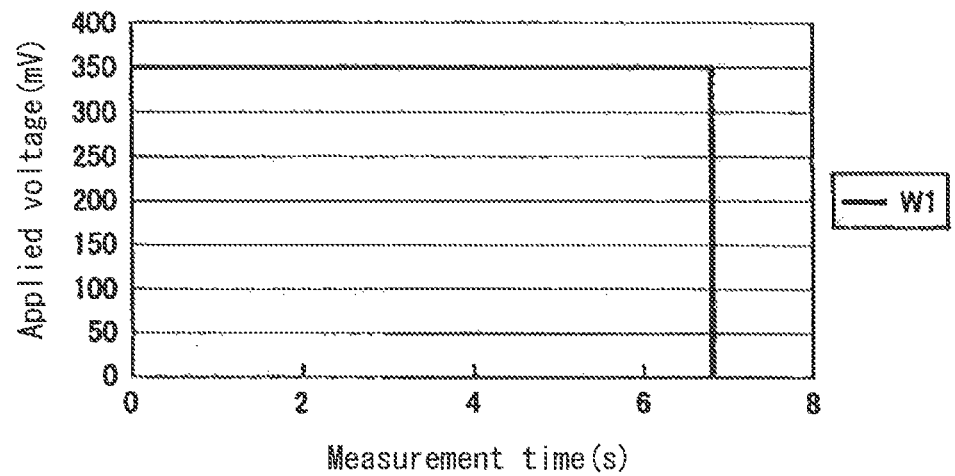
FIG. 7 shows an operation of a measuring device to apply a voltage to a biosensor according to an embodiment of the present invention.
Figure 7:
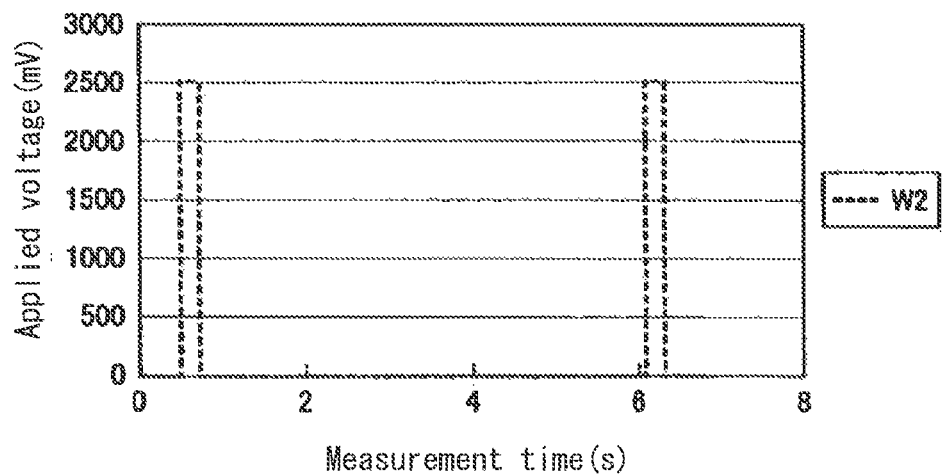

The measuring device 6 of this embodiment obtains a plurality of glucose response values and a plurality of blood cell amount response values by the operations described with reference to, e.g., FIGS. 7 and 8. Moreover, the measuring device 6 refers to the glucose concentration conversion matrices shown in FIGS. 9 to 12 and can convert the glucose response values and the blood cell amount response values into glucose conversion values and blood cell amount conversion values.

To measure the glucose concentration, the measuring device 6 applies a first voltage shown in FIG. 7A between the glucose working electrode 21 and the glucose counter electrode 22. For example, the CPU 72 applies a first voltage of 350 mV between the glucose working electrode 21 and the glucose counter electrode 22. As shown in FIG. 7A, the first voltage is continuously applied over a predetermined period in which the glucose concentration is being measured. Alternatively, the first voltage may be intermittently applied only at the predetermined timing of the measurement of the glucose response value, instead of the continuous application. The predetermined period may be, e.g., 0 to 7 seconds.

To measure the blood cell amount, the measuring device 6 applies a second voltage shown in FIG. 7B between the blood cell amount working electrode 23 and the blood cell amount counter electrode 24. For example, the CPU 72 applies a second voltage of 2500 mV between the blood cell amount working electrode 23 and the blood cell amount counter electrode 24. However, the second voltage is not limited thereto as long as the blood cell amount can be measured. As shown in FIG. 7B, the second voltage is applied at least twice, i.e., in the first half and the second half of the predetermined period.

Figure 8:
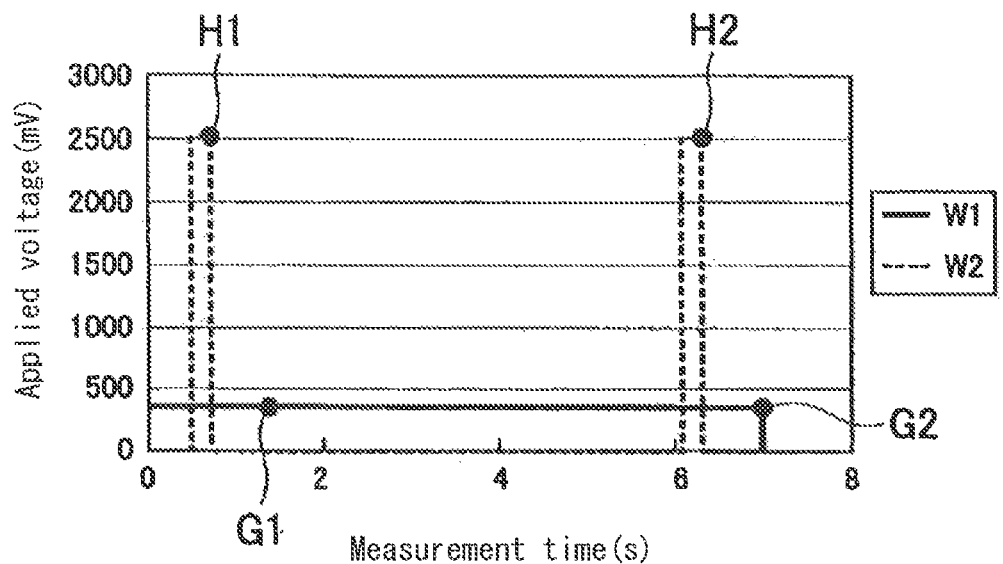
FIG. 8 is a diagram showing the timing of the measurement of the glucose response value and the blood cell amount response value by a measuring device according to an embodiment of the present invention.

The CPU 72 applies both the first voltage and the second voltage shown in FIGS. 7A and 7B to the biosensor 1, and then acquires the glucose response values and the blood cell amount response values at timing shown in FIG. 8. The CPU 72 acquires the glucose response value twice, i.e., in a first period included in the first half of the predetermined period and in a second period included in the second half of the predetermined period. Consequently, the CPU 72 can acquire a glucose response value G1 and a glucose response value G2. Moreover, the CPU 72 acquires the blood cell amount response value twice, i.e., in the first period included in the first half of the predetermined period and in the second period included in the second half of the predetermined period. Consequently, the CPU 72 can acquire a blood cell amount response value H1 and a blood cell amount response value H2.

It is desirable that the first period is set during which a change in temperature of the blood introduced into the biosensor 1 is large. Alternatively, it is preferable that the end point of the first period is set to the time at which a blood temperature difference is large when the biosensor 1 finishes the measurement. For example, the first period may be within a short period from the start of the measurement by the biosensor 1. In the example of FIG. 8, the first period may be within 1.5 seconds from the start of the measurement. It is desirable that the second period is set during which a change in temperature of the blood introduced into the biosensor 1 is stable. Alternatively, it is preferable that the start point of the second period is set to the time at which a blood temperature difference is small when the biosensor 1 finishes the measurement. For example, the second period may be within a short period from the end of the measurement by the biosensor 1. In the example of FIG. 8, the second period may be after 6 to 7 seconds from the measurement.

As described above, the measuring device 6 applies the first voltage to the first electrode pair of the glucose working electrode 21 and the glucose counter electrode 22 in the predetermined period, and detects an oxidation-reduction current corresponding to the blood component amount more than once at the predetermined timing of the measurement of the blood component amount. On the other hand, the measuring device 6 applies the second voltage within a predetermined short time before, during, or after the predetermined timing of the measurement of the blood component amount. Further, the measuring device 6 applies the second voltage in pulses to the second electrode pair of the blood cell amount working electrode 23 and the blood cell amount counter electrode 24 only at the timing of the measurement of the blood cell amount in the predetermined period, and detects a current corresponding to the blood cell amount.

When the two glucose response values G1, G2 and the two blood cell amount response values H1, H2 are measured, the CPU 72 refers to four glucose concentration conversion matrices and calculates the glucose conversion values and the blood cell amount conversion values. In this case, the four glucose concentration conversion matrices are prepared for each of the following combinations: the combination of the glucose response value G1 and the blood cell amount response value H1; the combination of the glucose response value G2 and the blood cell amount response value H1; the combination of the glucose response value G2 and the blood cell amount response value H1; and the combination of the glucose response value G2 and the blood cell amount response value H2.

Figure 9:
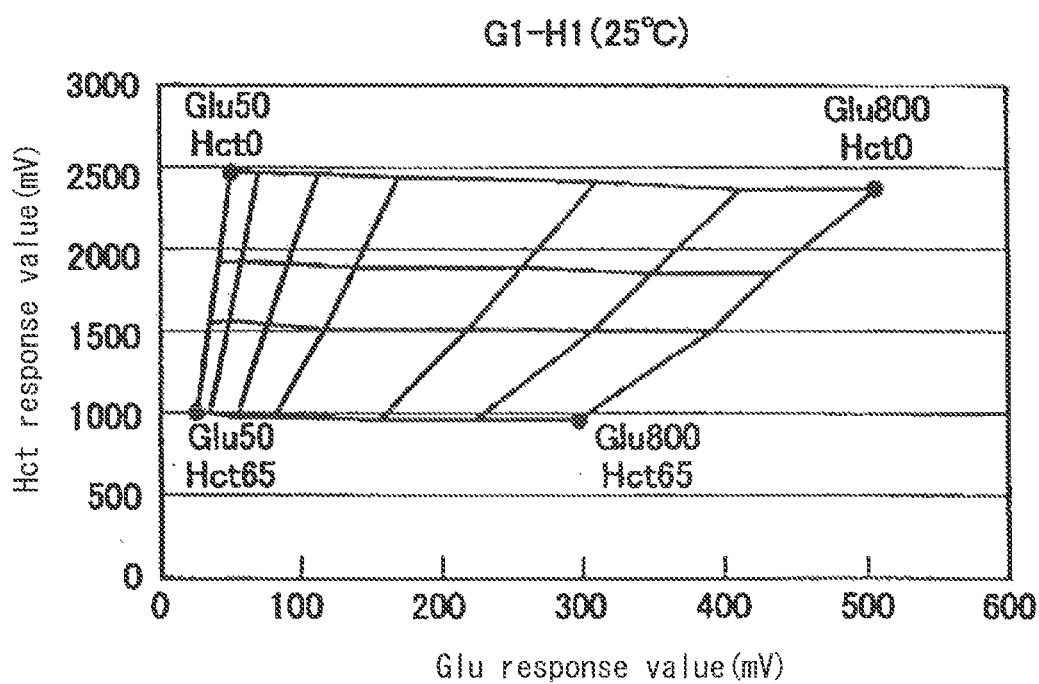
FIG. 9 is a diagram showing a glucose concentration conversion matrix calculated by a measuring device according to an embodiment of the present invention.
Figure 10:
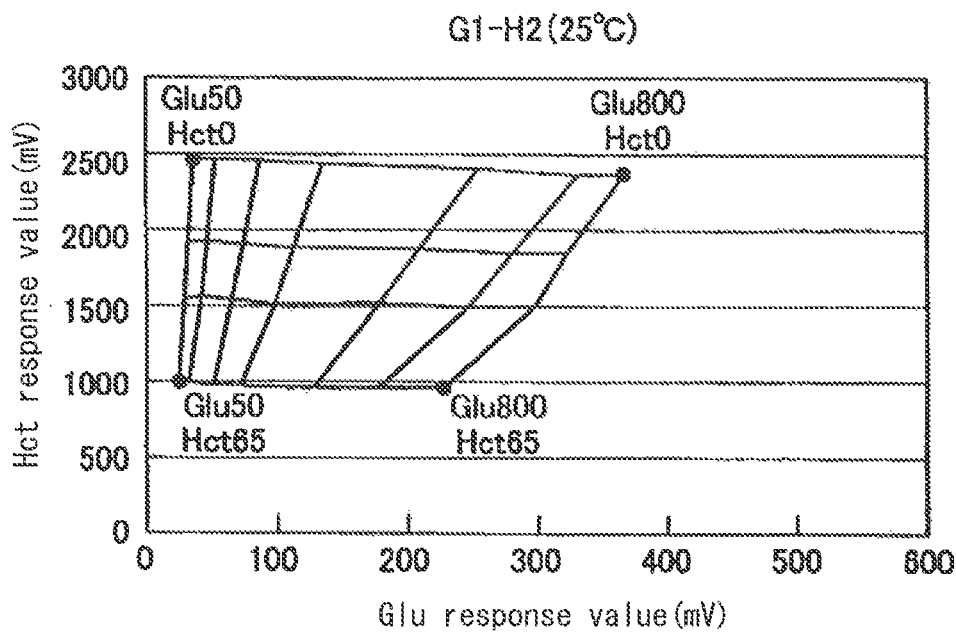
FIG. 10 is a diagram showing another glucose concentration conversion matrix calculated by a measuring device according to an embodiment of the present invention.
Figure 11:
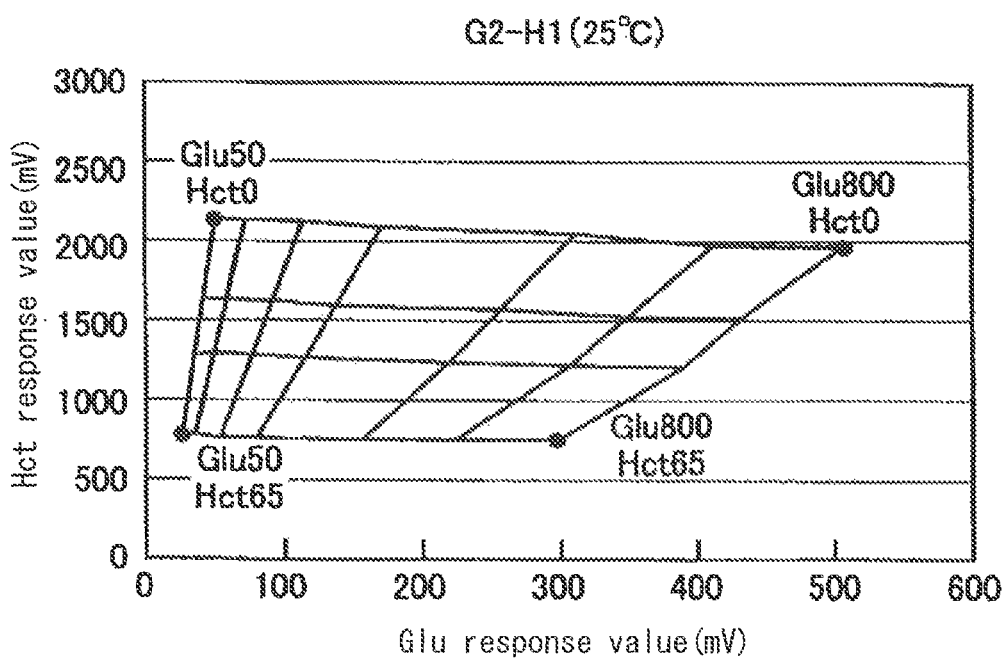
FIG. 11 is a diagram showing another glucose concentration conversion matrix calculated by a measuring device according to an embodiment of the present invention.
Figure 12:
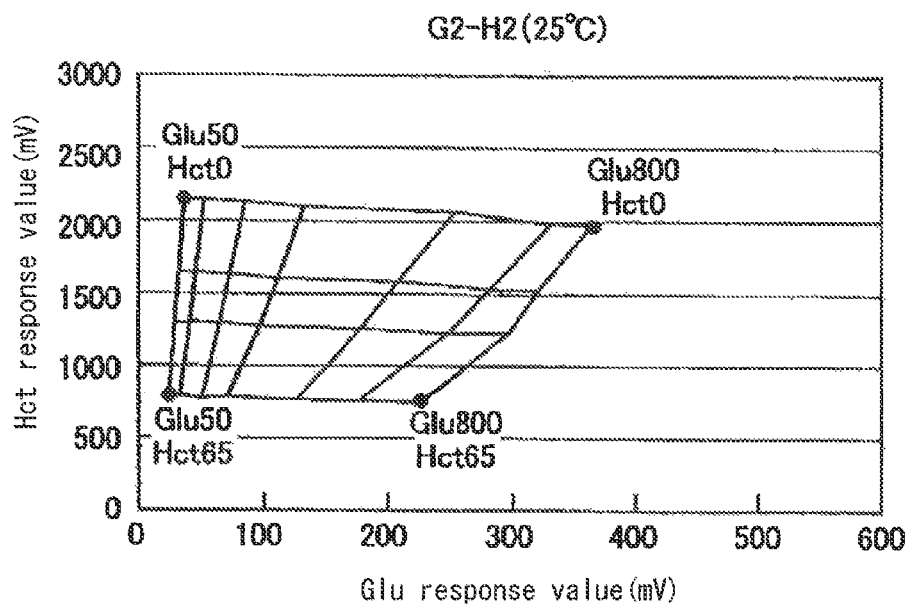
FIG. 12 is a diagram showing another glucose concentration conversion matrix calculated by a measuring device according to an embodiment of the present invention.

The CPU 72 uses the glucose concentration conversion matrix G1-H1 in FIG. 9 to convert the glucose response value G1 and the blood cell amount response value H1 of the measured data into a glucose conversion value and a blood cell amount conversion value. Similarly, the CPU 72 uses the glucose concentration conversion matrix G1-H2 in FIG. 10 to convert the glucose response value G1 and the blood cell amount response value H2 of the measured data into a glucose conversion value and a blood cell amount conversion value. Similarly, the CPU 72 uses the glucose concentration conversion matrix G2-H1 in FIG. 11 to covert the glucose response value G2 and the blood cell amount response value H1 of the measured data into a glucose conversion value and a blood cell amount conversion value. Similarly, the CPU 72 uses the glucose concentration conversion matrix G2-H2 in FIG. 12 to convert the glucose response value G2 and the blood cell amount response value H2 of the measured data into a glucose conversion value and a blood cell amount conversion value.

Specifically, in the measuring device 6, the data storage unit 74 stores the glucose concentration conversion matrices shown in FIGS. 9 to 12. The measuring device 6 measures the glucose response values and the blood cell amount response values of unknown blood, and acquires the measured data including a group of G1 and H1, a group of G1 and H2, a group of G2 and H1, and a group of G2 and H2. Then, the measuring device 6 plots the point determined by the combination of the glucose response value and the blood cell amount response value of the measured data on the corresponding glucose concentration conversion matrix, and converts the glucose response value and the blood cell amount response value into a glucose conversion value and a blood cell amount conversion value. Consequently, the measuring device 6 can obtain the glucose conversion value and the blood cell amount conversion value from each of the group of G1 and H1, the group of G1 and H2, the group of G2 and H1, and the group of G2 and H2.

Next, the measuring device 6 compares a plurality of groups of the glucose conversion values and the blood cell amount conversion values of the record data with a plurality of groups of the glucose conversion values and the blood cell amount conversion values of the measured data. As a result of the comparison, the measuring device 6 can correct the glucose conversion value of the measured data to the glucose conversion value of the record data that is closest to the measured data.

Figure 13:
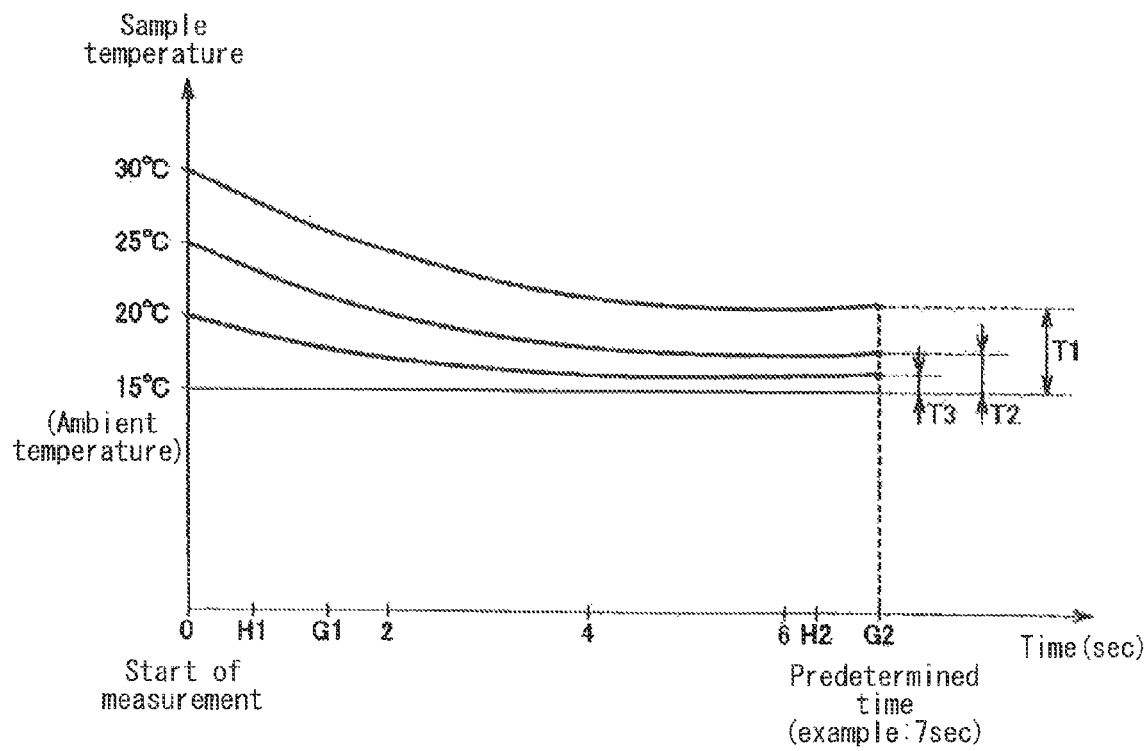
FIG. 13 is a diagram showing a change in temperature after a sample is introduced into a biosensor according to an embodiment of the present invention.

As shown in FIG. 13, the temperature of blood (sample) introduced into the biosensor 1 decreases with elapsed time after the introduction of the blood into the biosensor 1. As described above, when the measurement time (predetermined time) of the glucose concentration is 7 seconds, such a decrease in temperature of the blood over the measurement time differs depending on the blood temperature at the time of the introduction of the blood into the biosensor 1. The slope of a decrease in temperature of the blood increases with increasing the blood temperature at the time of the introduction of the blood into the biosensor 1. Moreover, the blood temperature at the end of the measurement time differs depending on the blood temperature at the time of the introduction of the blood into the biosensor 1. A difference between the blood temperature and the ambient temperature at the end of the measurement time increases as the blood temperature becomes higher when the blood is introduced into the biosensor 1. For example, when blood of 30° C. is introduced into the biosensor 1, a difference between the blood temperature and the ambient temperature at the end of the measurement time is T1. When blood of 25° C. is introduced into the biosensor 1, a difference between the blood temperature and the ambient temperature at the end of the measurement time is T2. When blood of 20° C. is introduced into the biosensor 1, a difference between the blood temperature and the ambient temperature at the end of the measurement time is T3.

Since the glucose response value and the blood cell amount response value measured by the measuring device 6 depend on the blood temperature, if the glucose response value and the blood cell amount response value are measured only at the end of the measurement time, it is not possible to obtain an accurate glucose response value and an accurate blood cell amount response value. Therefore, the measuring device 6 measures the glucose response value and the blood cell amount response value more than once in the measurement time, and obtains the glucose conversion values and the blood cell amount conversion values. Moreover, the measuring device 6 combines the glucose response values and the blood cell amount response values as desired, and obtains the desired combinations of the glucose conversion values and the blood cell amount conversion values.

In the measuring device 6, the data storage unit 74 stores the record data shown in, e.g., FIG. 14. This record data may be prepared in the following manner. For example, using blood with a glucose concentration of 100 mg/dl and a blood cell amount of 25%, the glucose response values and the blood cell amount response values are measured at each ambient temperature as well as at each sample introduction temperature. Then, the glucose conversion values are obtained for each of the above combinations. The sample introduction temperature does not need to be included in the record data. Specifically, in the record data, the ambient temperature A is associated with a glucose conversion value Aa1 obtained from the glucose concentration conversion matrix G1-H1 in FIG. 9, a glucose conversion value Aa2 obtained from the glucose concentration conversion matrix G1-H2 in FIG. 10, a glucose conversion value Aa3 obtained from the glucose concentration conversion matrix G2-H1 in FIG. 11, and a glucose conversion value Aa4 obtained from the glucose concentration conversion matrix G2-H2 in FIG. 12. It is desirable that the record data includes the glucose conversion values at a plurality of sample introduction temperatures for each ambient temperature. Moreover, it is desirable that the record data includes the glucose conversion values at each of a plurality of ambient temperatures.

The measuring device 6 can compare the glucose conversion values for each of the combinations of the glucose response values and the blood cell amount response values of the measured data with the glucose conversion values of the record data, and thus can determine the most approximate record data. Specifically, when the ambient temperature is about A, the measuring device 6 extracts the glucose conversion values Aa1 to Aa4, Ab1 to Ab4, and Ac1 to Ac4 for each of the combinations corresponding to the ambient temperature A. The measuring device 6 compares the glucose conversion values for each of the combinations of the measured data with the extracted glucose conversion values Aa1 to Aa4, Ab1 to Ab4, and Ac1 to Ac4. If the glucose conversion values for each of the combinations of the measured data are closely approximated to the glucose conversion values Aa1 to Aa4, Ab1 to Ab4, and Ac1 to Ac4, then the measuring device 6 can correct the glucose conversion value of the measured data to 100 mg/dl.

As described above, the measuring device 6 converts the measured glucose response values and the measured blood cell amount response values into a plurality of glucose conversion values and a plurality of blood cell amount conversion values. Based on the glucose conversion values and the blood cell amount conversion values, the measuring device 6 can correct the glucose conversion value of the measured data. Thus, this biosensor system can suppress the measurement error of the glucose concentration compared to the use of the current value generated by the oxidation-reduction reaction.

The glucose conversion values of the measured data differ depending on the ambient temperature of the biosensor 1. For example, assuming that the glucose concentration conversion matrices in FIGS. 9 to 12 are prepared at an environmental temperature of 25° C., blood with a glucose concentration of 125 mg/dl is measured at an ambient temperature of 25° C. in the biosensor 1, and the glucose conversion values are calculated from the glucose response values G1, G2 and the blood cell amount response values H1, H2. As shown in FIG. 15, the resultant glucose conversion values of all the combinations are 125 mg/dl. However, if the ambient temperature of the biosensor 1 is changed to 35° C., the glucose conversion values of all the combinations are different.

When the blood cell amount is changed, the glucose conversion values of the measured data can vary by the degree of the influence shown in, e.g., FIG. 16. If the blood cell amount is changed by 25%, the glucose conversion values vary by 20% with a glucose concentration of 100 mg/dl. Moreover, the glucose conversion values vary by 25% with a glucose concentration of 200 mg/di, and the glucose conversion values vary by 21% with a glucose concentration of 110 mg/dl.

Figures 17, 18:
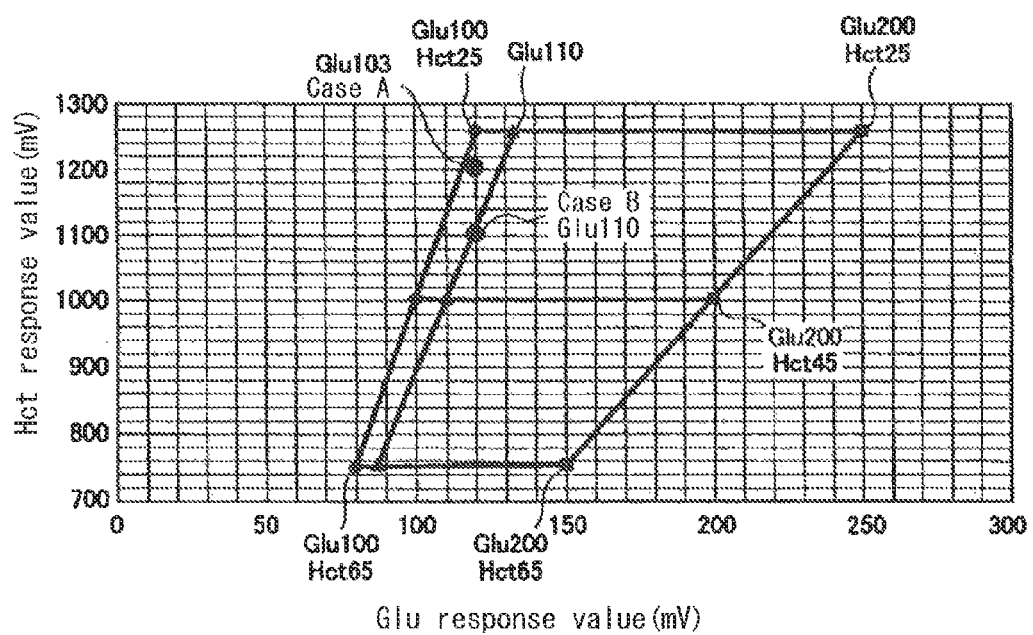
FIG. 17 is a diagram showing the relationship between the known glucose concentration, the known blood cell amount, the degree of the influence of temperature, the glucose response value, and the blood cell amount response value when the temperature is changed in a measuring device according to an embodiment of the present invention.
FIG. 18 is a diagram showing the relationship between the glucose response value and the blood cell amount response value when they are affected by the temperature in a measuring device according to an embodiment of the present invention.

When the ambient temperature of the biosensor 1 is changed, as shown in FIG. 17, even if blood has a known glucose concentration of 100 mg/dl and a known blood cell amount response value of 1000 mV, both the glucose response value and the blood cell amount response value measured can vary due to the degree of the influence of temperature.

As described above, the glucose conversion values differ depending on the ambient temperature. Moreover, the glucose response values vary with the ambient temperature and the blood cell amount. Therefore, even if blood with the same glucose concentration is measured to calculate the glucose response values and the blood cell amount response values, the glucose conversion values differ depending on the cases A, B to be measured, as shown in FIG. 18. In the case A, the glucose conversion value is 103 mg/dl. In the case B, the glucose conversion value is 110 mg/dl.

Thus, in the measuring device 6, it is desirable that the data storage unit 74 stores the record data at each ambient temperature in view of the influence of the ambient temperature on the glucose response values and the blood cell amount response values. The measuring device 6 extracts the record data closer to the current ambient temperature from the record data stored in the data storage unit 74. The measuring device 6 compares the glucose conversion values included in the record data that has been extracted in accordance with the current ambient temperature with the glucose conversion values of the measured data. Thus, the measuring device 6 can correct the glucose conversion value of the measured data to the glucose conversion value of the most approximate record data.

As described above, the blood temperature in the biosensor 1 is changed from the time of the introduction of the blood to the end of the measurement, and the glucose response value varies with the blood cell amount. Therefore, as described above, it is desirable that the measuring device 6 makes any combinations of a plurality of glucose response values and a plurality of blood cell amount response values measured during the predetermined measurement time, and then calculates the glucose conversion values. Thus, even if the blood temperature is changed and the blood cell amount is unknown, as described above, the measuring device 6 can calculate the glucose conversion values from any combinations of the glucose response values and the blood cell amount response values, and can select the record data that is closely approximated to the glucose conversion value of the measured data.

Specifically, the measuring device 6 measures the glucose response value and the blood cell amount response value in the first period included in the first half of the predetermined period and in the second period included in the second half of the predetermined period. Therefore, the measuring device 6 can acquire the glucose response value and the blood cell amount response value both when a change in temperature is large and when a change in temperature is stable. Thus, even if the blood temperature is changed differently every time the measurement is performed, the measuring device 6 can obtain the glucose conversion values and the blood cell amount conversion values of the measured data in a plurality of periods, and can correct them with the record data. This can reduce the disadvantage that the glucose conversion values vary with blood temperature changes so that accurate glucose conversion values cannot be obtained.

Figure 19:
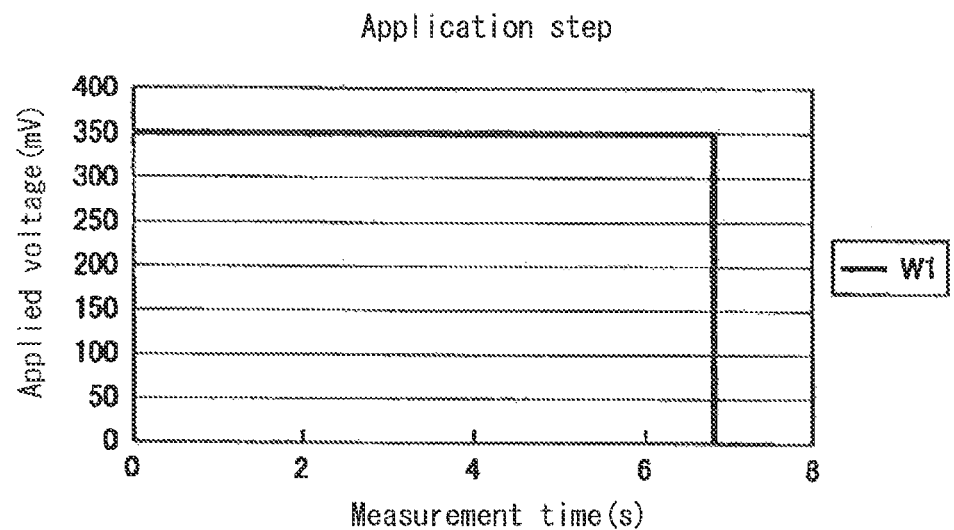
FIG. 19 shows another operation of a measuring device to apply a voltage to a biosensor according to an embodiment of the present invention.
Figure 19:
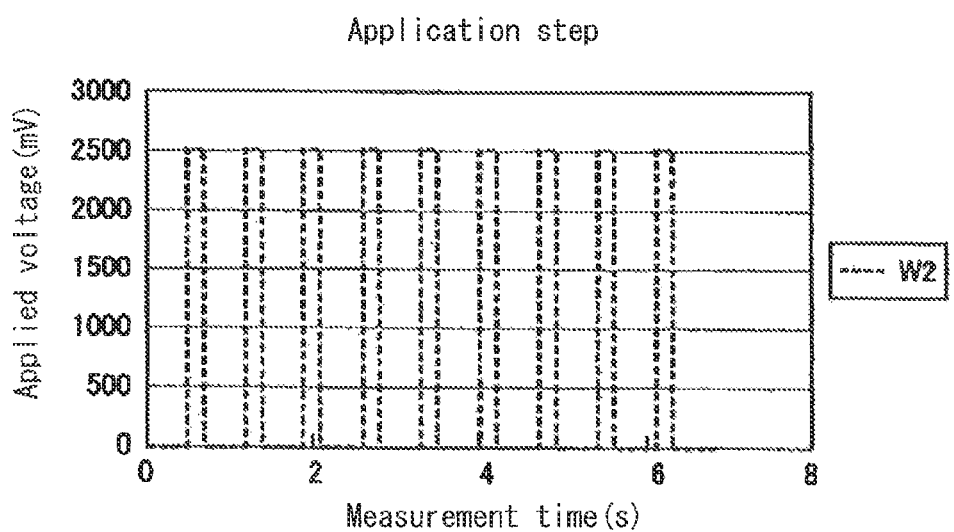

It is desirable that the measuring device 6 performs the measurement as many as possible during the predetermined period in order to improve the correction accuracy of the measured data. For example, the first voltage is applied to the biosensor 1 to measure the glucose response values, as shown in FIG. 19A, and the second voltage is applied to the biosensor 1 to measure the blood cell amount response values, as shown in FIG. 19B. The measuring device 6 acquires the blood cell amount response values and the glucose response values at the measurement points shown in FIG. 20. Thus, the measuring device 6 can obtain 9 glucose response values and 9 blood cell amount response values within the predetermined period.

Figure 21:
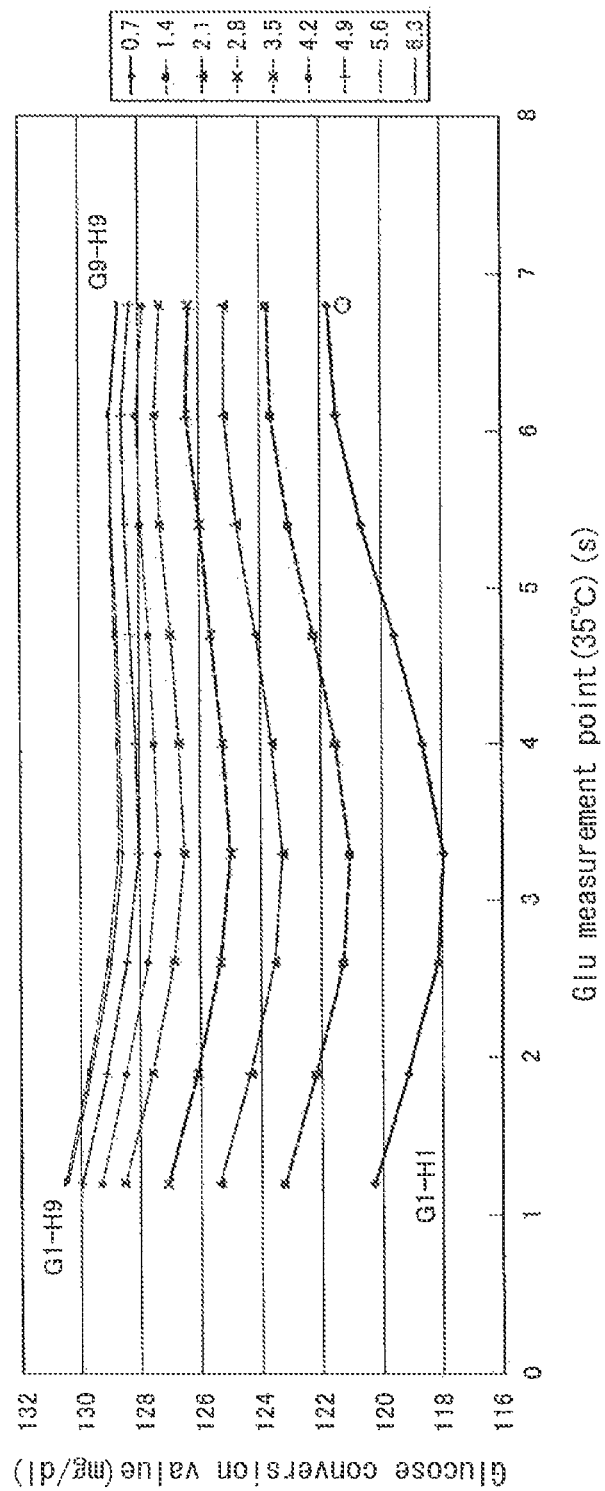
FIG. 21 is a diagram showing the relationship between a measurement point of the glucose response value and the glucose conversion value in a measuring device according to an embodiment of the present invention.

The measuring device 6 combines the 9 glucose response values and the 9 blood cell amount response values to make 81 groups of the glucose response values and the blood cell amount response values. In other words, the measuring device 6 combines the glucose response values G1 to G9 with the blood cell amount response values H1 to H9. Therefore, the measuring device 6 can obtain a glucose conversion value from G1-H1, . . . , and a glucose conversion value from G1-H9, as shown in FIG. 21. Similarly, the measuring device 6 can obtain a plurality of glucose conversion values from the combinations of G2 and H1 to H9, . . . , and a plurality of glucose conversion values from the combinations of G9 and H1 to H9. Thus, the measuring device 6 compares 81 glucose conversion values of the measured data with 81 glucose conversion values of the record data, and can select the record data that is most closely approximated to the measured data. Accordingly, the measuring device 6 can correct the glucose conversion value of the measured data to the glucose conversion value of the record data obtained using the 81 glucose conversion values.

As described above, the record data is prepared to include many combinations of the glucose conversion values and the blood cell amount conversion values, and the same combinations of the glucose conversion values and the blood cell amount conversion values of the measured data as those of the record data can be used to correct the measured data. Therefore, even if the glucose conversion values vary with blood temperature changes, the ambient temperature, and the blood cell amount, as described above, since many combinations of the glucose conversion values and the blood cell amount conversion values are used, the measured data can be corrected to the glucose conversion value with less error.

Next, another embodiment that differs from the above embodiment will be described.

Figure 22:
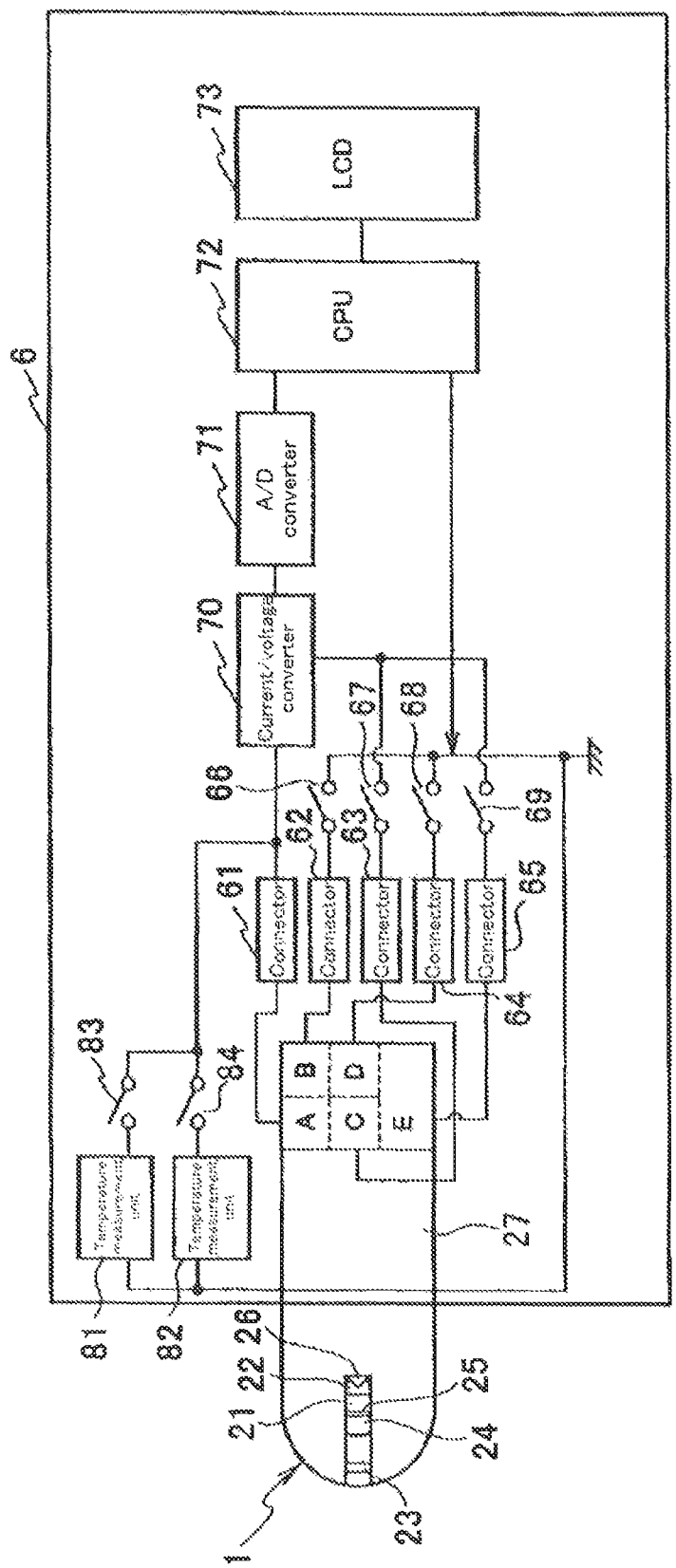
FIG. 22 is a block diagram showing another configuration of a measuring device according to an embodiment of the present invention.

A measuring device 6 of this embodiment performs a multivariate analysis with the use of at least a part of the measured glucose conversion values and the measured blood cell amount conversion values, and then corrects the glucose repose values measured within a predetermined period. This measuring device 6 differs from the measuring device 6 of the above embodiment in that the data storage unit 74 is not provided, as shown in FIG. 22.

Similarly to the above embodiment, the measuring device 6 measures a plurality of glucose response values and a plurality of blood cell amount response values. The CPU 72 performs the multivariate analysis by using a part or the whole of the measured glucose response values and the measured blood cell amount response values, and obtains the final glucose conversion value. The measuring device 6 may perform, e.g., a multiple regression analysis as the multivariate analysis. The multiple regression analysis uses as a response function, e.g., the following multiple regression equation of a linear polynomial:

Glucose conversion value=$a \times G1 + b \times H1 + c \times G2 + \ldots + n \times Gn + (n+1) \times Hn + Co$, where Co represents a constant, a, b, c, . . . , n represent coefficients by which the glucose response values are multiplied, Gn represents a glucose response value, and Hn represents a blood cell amount response value. In this multiple regression analysis, a known glucose concentration is used as a target value, and the process of determining the coefficients of the multiple regression equation is performed. The CPU 72 determines the coefficients (a, b, c, . . . , n) of the multiple regression equation, by which one or more glucose response values are multiplied, based on the results of the measurement of the glucose response values G1 to G9 in combination with the blood cell amount response values H1 to H9 at different ambient temperatures and different sample introduction temperatures under the conditions that the ambient temperature and the sample introduction temperature are variously controlled. This can provide the response function that serves as a correction factor for the influence of temperature during the measurement and incorporates the ambient temperature and the sample introduction temperature. Thus, the CPU 72 performs the regression analysis to determine a correction formula that corrects the difference between an intermediate conversion value and the known value to zero. The intermediate conversion value is obtained using each of the glucose response values and the blood cell amount response values.

As described above, the measuring device 6 of this embodiment converts the glucose response values and the blood cell amount response values into the glucose conversion values and the blood cell amount conversion values, and then can determine the final glucose concentration by the operation (correction operation) of the multiple regression analysis. Thus, the measuring device 6 can suppress the measurement error of the glucose concentration, compared to the case where the glucose response values themselves are used to obtain the glucose concentration.

The value determined by the multiple regression analysis is not limited to the glucose conversion value and may be, e.g., the amount of correction of the glucose conversion value.

The multiple regression analysis may also use as a response function, e.g., the following multiple regression equation of a quadratic polynomial.

[Formula 1]

$$\text{Glucose conversion value} = \beta_0 + \sum_{i=1}^{k} \beta_i x_i + \sum_{i=1}^{k} \beta_{ii} x_i^2 + \sum_{i<j} \beta_{ij} x_i x_j$$

In the quadratic polynomial, any combination of the glucose response values (G1 to Gm, where m represents the number of numerical values to be measured) and the blood cell response values (H1 to Hp, where p represents the number of numerical values to be measured) can be assigned to each of the variables xi. Like the linear polynomial, the coefficients of the quadratic polynomial are determined by the learning process.

In the quadratic polynomial, when a total of 18 groups of the glucose response values and the blood cell response values are selected to form a glucose concentration conversion formula or a correction formula, the number of terms of the correction formula is 190 (including a constant term).

In determining the coefficients actually, higher-order terms ($xi^2$, xixj, etc.) may be reduced to first-order terms containing parameters by a change of variables. Therefore, the actual calculation to determine the coefficients becomes the same as that in the linear polynomial. The variables of the quadratic polynomial may include the ambient temperature measured by the measuring device 6 in addition to the glucose response values and the blood cell response values.

When the glucose concentration conversion formula or the correction formula is expressed as a quadratic polynomial, it is likely to reduce the error in the actual distribution of the terms compared to the linear polynomial.

The above quadratic polynomial is equal to an approximate function obtained by the Taylor expansion of a hypersurface up to second order. The hypersurface defines a distribution in a multidimensional space using the variables (e.g., the glucose response values and the blood cell response values incorporated into the correction formula) as axes. As long as it is theoretically confirmed that the estimated distribution is continuous, if regions of the variables (the selected group of glucose response values and the selected group of blood cell response values) are sufficiently narrow, high accuracy can be achieved in principle. Although higher-order variables may be used, when the response values with the same quantity are combined, the number of terms of the glucose conversion formula or the correction formula is increased. This leads to the disadvantages of making the computation more complicated, and increasing the minimum number of data required to determine the coefficients.

The above example uses the linear regression equation as a form of the glucose conversion formula or the correction formula. However, the regression equation does not necessarily need to be linear. For example, the variables xi (including the glucose response values, the blood cell response values, and the ambient temperature) may be combined with operators to form terms, and the terms may be linearly added. In this case, when the regression analysis is performed to determine the coefficients of the terms, each of the terms is reduced to a linear equation with parameters by a change of variables, as in the case of the linear polynomial and the quadratic polynomial. Thus, the technique of the multiple regression analysis of the linear polynomial can be applied to the present invention.

The above embodiments are merely an example of the present invention. Therefore, the present invention is not limited to the above embodiments, and it is to be understood that various modifications may be introduced in accordance with the design or the like into any embodiment other than the above without departing from the technical idea of the present invention.

DESCRIPTION OF REFERENCE NUMERALS

1 Biosensor
2 Blood component measurement layer
6 Measuring device
21 Glucose working electrode (first electrode pair, blood component amount measuring pair)
22 Glucose counter electrode (first electrode pair, blood component amount measuring electrode pair)
23 Blood cell amount working electrode (second electrode pair, blood cell amount measuring electrode pair)
24 Blood cell amount counter electrode (second electrode pair, blood cell amount measuring electrode pair)
25 Non-interacting portion
26 Detecting electrode
72 CPU (blood component amount measurement means, blood cell amount measurement means, measurement control means, blood component amount correction means)
74 Data storage unit (storage means)
81, 82 Temperature measurement unit

The invention claimed is:

1. A blood component measuring device that measures a blood component amount with a biosensor in which blood is introduced, and a blood component contained in the blood is oxidized and reduced by an oxidoreductase,
the device comprising:
a blood component amount measurement means that detects an oxidation-reduction current generated by the oxidation-reduction when a first voltage is applied to a first electrode pair of the biosensor, and that converts the oxidation-reduction current into the blood component amount;
a blood cell amount measurement means that detects a current generated when a second voltage is applied to a second electrode pair of the biosensor, and that converts the detected current into a blood cell amount contained in the blood;
a measurement control means that controls the blood component amount measurement means to apply the first voltage to the first electrode pair, to detect an oxidation-reduction current corresponding to the blood component amount more than once at predetermined timing of measurement of the blood component amount, and thus to measure the blood component amount more than once within a predetermined period after the introduction of the blood into the biosensor, and that also controls the blood cell amount measurement means to apply the second voltage in pulses to the second electrode pair within a predetermined short time before, during, or after the predetermined timing of the measurement of the blood component amount and only at timing of measurement of the blood cell amount in the predetermined period, to detect a current corresponding to the blood cell amount, and thus to measure the blood cell amount more than once within the predetermined period; and
a blood component amount correction means that corrects the blood component amount measured by the blood component amount measurement means based on at least a part of a plurality of blood component amounts measured by the blood component amount measurement means and a plurality of blood cell amounts measured by the blood cell amount measurement means under the control of the measurement control means.

2. The blood component measuring device according to claim 1, comprising:
a storage means that stores record data including a plurality of blood component amounts and a plurality of blood cell amounts that are converted from the respective currents detected more than once within the predetermined period for each blood with a known blood component amount and a known blood cell amount,
wherein the blood component amount correction means compares (i) the record data including a blood component amount that is closely approximated to any blood component amount of the plurality of blood component amounts measured and the plurality of blood cell amounts measured with (ii) measured data including the plurality of blood component amounts measured by the blood component amount measurement means and the plurality of blood cell amounts measured by the blood cell amount measurement means, and then the blood component amount correction means corrects the measured blood component amount to the blood component amount of blood having the record data that is most closely approximated to the measured data.

3. The blood component measuring device according to claim 2, wherein the blood component amount correction means compares (i) any combination of a blood component amount and a blood cell amount in the plurality of blood component amounts and the plurality of blood cell amounts measured under the control of the measurement control means with (ii) the record data including the same combination of a blood component amount and a blood cell amount in the plurality of blood component amounts and the plurality of blood cell amounts stored in the storage means, and then the blood component amount correction means corrects the measured blood component amount to the blood component amount of blood having the most approximate record data.

4. The blood component measuring device according to claim 2, wherein the measurement control means controls the blood component amount measurement means to measure the blood component amount in a first period included in a first half of the predetermined period and in a second period included in a second half of the predetermined period.

5. The blood component measuring device according to claim 4, wherein the measurement control means controls the blood component amount measurement means to measure the blood component amount at least in a first period of the predetermined period during which a change in temperature of the blood introduced into the biosensor is large and in a second period of the predetermined period during which a change in temperature of the blood introduced into the biosensor is stable.

6. The blood component measuring device according to claim 4, wherein the measurement control means controls the blood cell amount measurement means to measure the blood cell amount at least in the first period and in the second period, during each of which the blood component amount is measured by the blood component amount measurement means.

7. The blood component measuring device according to claim 4, wherein the record data and the measured data include a group of the blood component amount measured in the first period and the blood cell amount measured in the first period, a group of the blood component amount measured in the first period and the blood cell amount measured in the second period, a group of the blood component amount measured in the second period and the blood cell amount measured in the first period, and a group of the blood component amount measured in the second period and the blood cell amount measured in the second period, and
wherein the blood component amount correction means compares the same group between the record data and the measured data.

8. The blood component measuring device according to claim 1, comprising:
a storage means that stores record data including a plurality of blood component amounts and a plurality of blood cell amounts that are converted from the respective currents detected more than once within the predetermined period for each blood with a known blood component amount and a known blood cell amount and for each ambient temperature; and
a temperature detection means that detects an ambient temperature,
wherein the blood component amount correction means extracts record data with a temperature closer to the ambient temperature detected by the temperature detection means, and compares the extracted record data with measured data including the plurality of blood component amounts measured by the blood component amount measurement means and the plurality of blood cell amounts measured by the blood cell amount measurement means, and then the blood component amount correction means corrects the measured blood component amount to the blood component amount of blood having the record data that is most closely approximated to the measured data.

9. The blood component measuring device according to claim 1, wherein the blood component amount correction means performs a multivariate analysis with the use of at least a part of the plurality of blood component amounts and the plurality of blood cell amounts to correct the blood component amount measured by the blood component amount measurement means.

10. The blood component measuring device according to claim 1, wherein the measurement control means allows the second voltage to be applied to the second electrode pair only at the timing of the measurement of the blood cell amount in the predetermined period while the first voltage is being applied to the first electrode pair.

11. A method for measuring a blood component that measures a blood component amount with a biosensor in which blood is introduced, and a blood component contained in the blood is oxidized and reduced by an oxidoreductase,
the method comprising the following steps of:
(i) detecting an oxidation-reduction current generated by the oxidation-reduction when a first voltage is applied to a first electrode pair of the biosensor, and converting the oxidation-reduction current into the blood component amount; and
(ii) detecting a current generated when a second voltage is applied to a second electrode pair of the biosensor, and converting the detected current into a blood cell amount contained in the blood,
wherein the blood component amount is measured more than once within a predetermined period after the introduction of the blood into the biosensor by applying the first voltage to the first electrode pair, and detecting an oxidation-reduction current corresponding to the blood component amount more than once at predetermined timing of measurement of the blood component amount, and the blood cell amount is also measured more than once within the predetermined period by applying the second voltage in pulses to the second electrode pair within a predetermined short time before, during, or after the predetermined timing of the measurement of the blood component amount and only at timing of measurement of the blood cell amount in the predetermined period, and detecting a current corresponding to the blood cell amount, and
wherein the measured blood component amount is corrected based on at least a part of the plurality of blood component amounts measured and the plurality of blood cell amounts measured.

12. The method for measuring a blood component according to claim 11, comprising:
referring to record data including a plurality of blood component amounts and a plurality of blood cell amounts that are converted from the respective currents detected more than once within the predetermined period for each blood with a known blood component amount and a known blood cell amount stored in a storage means;
comparing (i) the record data including a blood component amount that is closely approximated to any blood component amount of the plurality of blood component amounts measured and the plurality of blood cell amounts measured with (ii) measured data including the plurality of blood component amounts measured and the plurality of blood cell amounts measured; and
correcting the measured blood component amount to the blood component amount of blood having the record data that is most closely approximated to the measured data.

13. The method for measuring a blood component according to claim 12, comprising:

comparing (i) any combination of a blood component amount and a blood cell amount in the plurality of blood component amounts measured and the plurality of blood cell amounts measured with (ii) the record data including the same combination of a blood component amount and a blood cell amount in the plurality of blood component amounts and the plurality of blood cell amounts stored in the storage means; and correcting the measured blood component amount to the blood component amount of blood having the most approximate record data.

14. The method for measuring a blood component according to claim 12, comprising:

measuring the blood component amount in a first period included in a first half of the predetermined period and in a second period included in a second half of the predetermined period.

15. The method for measuring a blood component according to claim 14, comprising:

measuring the blood component amount at least in a first period of the predetermined period during which a change in temperature of the blood introduced into the biosensor is large and in a second period of the predetermined period during which a change in temperature of the blood introduced into the biosensor is stable.

16. The method for measuring a blood component according to claim 14, comprising:

measuring the blood cell amount at least in the first period and in the second period.

17. The method for measuring a blood component according to claim 14, wherein the record data and the measured data include a group of the blood component amount measured in the first period and the blood cell amount measured in the first period, a group of the blood component amount measured in the first period and the blood cell amount measured in the second period, a group of the blood component amount measured in the second period and the blood cell amount measured in the first period, and a group of the blood component amount measured in the second period and the blood cell amount measured in the second period, and wherein the blood component amount is corrected by comparing the same group between the record data and the measured data.

18. The method for measuring a blood component according to claim 11, comprising:

referring to record data including a plurality of blood component amounts and a plurality of blood cell amounts that are converted from the respective currents detected more than once within the predetermined period for each blood with a known blood component amount and a known blood cell amount and for each ambient temperature stored in a storage means;

detecting an ambient temperature;

extracting record data with a temperature closer to the detected ambient temperature, and comparing the extracted record data with measured data including the plurality of blood component amounts measured and the plurality of blood cell amounts measured; and correcting the measured blood component amount to the blood component amount of blood having the record data that is most closely approximated to the measured data.

19. The method for measuring a blood component according to claim 11, comprising:

performing a multivariate analysis with the use of at least a part of the plurality of blood component amounts and the plurality of blood cell amounts to correct the blood component amount measured within the predetermined period.

20. The method for measuring a blood component according to claim 11, wherein the second voltage is applied to the second electrode pair only at the timing of the measurement of the blood cell amount in the predetermined period while the first voltage is being applied to the first electrode pair.

* * * * *